United States Patent [19]

Fujimoto et al.

[11] Patent Number: 5,436,391
[45] Date of Patent: Jul. 25, 1995

[54] SYNTHETIC INSECTICIDAL GENE, PLANTS OF THE GENUS ORYZA TRANSFORMED WITH THE GENE, AND PRODUCTION THEREOF

[75] Inventors: Hideya Fujimoto, Tokyo; Kimiko Ito, Yokohama, both of Japan; Mikihiro Yamamoto, Davis, Calif.; Ko Shimamoto, Kawasaki, Japan

[73] Assignees: Mitsubishi Corporation; Mitsubishi Kasei Corporation, both of Tokyo, Japan

[21] Appl. No.: 982,712

[22] Filed: Nov. 27, 1992

[30] Foreign Application Priority Data

Nov. 29, 1991 [JP] Japan ................................. 3-340059

[51] Int. Cl.$^6$ .......................... A01H 4/00; C12N 15/32
[52] U.S. Cl. ............................ 800/205; 800/DIG. 57; 536/23.71; 435/320.1; 435/172.3; 435/240.47
[58] Field of Search ...................... 800/205, DIG. 57; 536/23.71; 435/320.1, 172.3, 240.4, 240.47; 935/35, 67

[56] References Cited

FOREIGN PATENT DOCUMENTS

| | | |
|---|---|---|
| 142924 | 5/1985 | European Pat. Off. . |
| 193259 | 9/1986 | European Pat. Off. . |
| 213818 | 3/1987 | European Pat. Off. . |
| 224331 | 6/1987 | European Pat. Off. . |
| 228838 | 7/1987 | European Pat. Off. . |
| 269601 | 6/1988 | European Pat. Off. . |
| 289479 | 11/1988 | European Pat. Off. . |
| 303426 | 2/1989 | European Pat. Off. . |
| 339009 | 10/1989 | European Pat. Off. . |
| 0359472 | 3/1990 | European Pat. Off. . |
| 359472 | 3/1990 | European Pat. Off. . |
| 400246 | 12/1990 | European Pat. Off. . |
| 462721 | 12/1991 | European Pat. Off. . |
| WO86/01536 | 3/1986 | WIPO . |
| WO88/08034 | 10/1988 | WIPO . |
| WO90/10076 | 9/1990 | WIPO . |
| 9010076 | 9/1990 | WIPO . |
| WO91/14778 | 10/1991 | WIPO . |
| WO91/16432 | 10/1991 | WIPO . |
| WO91/16433 | 10/1991 | WIPO . |
| WO91/16434 | 10/1991 | WIPO . |
| WO91/18094 | 11/1991 | WIPO . |

OTHER PUBLICATIONS

Christore, et al (Oct. 1991) Biol Technology 9:957–962.
Raineri, et al. (Jan. 1990) Biol Technology 8: 33–38.
Geiser, et al (1986) Gene 48: 109–118.
Vaeck et al., *Nature* 328, 33–37 (1987).
Fischhoff et al., *Bio/Technology*, 5, 807–813 (1987).
Barton et al., *Plant Physiol.*, 85, 1103–1109 (1987).
Perlak et al., *Bio/Technology*, 8, 939–943 (1990).
Murray et al., *Plant Molecular Biology*, 16, 1035–1050 (1991).
Perlak et al., *Proc. Natl. Acad. Sci. USA*, 88, 3324–3328 (1991).
Wong et al., *Plant Molecular Biology*, 20, 81–93 (1992).
Cheng et al., *Plant Science*, 81, 83–91 (1992).
Carozzi et al., *Plant Molecular Biology*, 20, 539–548 (1992).
Williams et al., *Bio/Technology*, 10, 540–543 (1992).

*Primary Examiner*—Che S. Chereskin
*Attorney, Agent, or Firm*—Wenderoth, Lind & Ponack

[57] ABSTRACT

A synthetic gene encoding an insecticidal protein, the gene is provided having a base sequence which has been modified to bring the codon usage in conformity with the genes of gramineous plants particularly rice plants. A preferred gene sequence is shown in SEQ ID NO: 1. An expression vector containing said structural gene is provided. A method for producing recombinant gramineous plants is provided, which comprises transforming protoplasts derived from gramineous plants with the vector, incubating the protoplasts in a liquid medium in the presence of cultured cells of the plants to form colonies and regenerating plants from said colonies. Recombinant gramineous plants having resistance against insects are also provided.

4 Claims, 23 Drawing Sheets

FIG. 7

```
                                              PRIMER 2-1
     910        920        930        940         950        960
AACAGCATCA CCATCTACAC CGACGCCCAC AGGGGGCG AGT ACT ACTGGTC CGGCCACCAG
                                          ScaI
                                            ↑
     970        980        990       1000        1010       1020
ATCATGGCCT CCCCGGTCGG CTTCTCCGGC CCGGAGTTCA CCTTCCCGCT CTACGGCACG
                                            PRIMER 2-2
    1030       1040       1050       1060        1070       1080
ATGGGCAACG CCGCCCCGCA GCAACGCATC GTCGCCCAGC TCGGGCCAGGG CGTCTACAGG
                              PRIMER 2-4
                                ↓
    1090       1100       1110       1120        1130       1140
ACCCTCAGCT CCACCCTCTA CAGG AGGCCT TTCAACATCG GCATCAACAA CCAGCAGCTC
                              StuI   PRIMER 2-3
                                           ↑
    1150       1160       1170       1180        1190       1200
TCCGTCCTCG ACGGCACCGA GTTCGCCTAC GGCACCTCCT CCAACTTGCC GTCCGCCGTC
                                 PRIMER 2-5
                                     ↑
    1210       1220       1230       1240        1250       1260
TACAGGAAGA GCGGCACCGT GGACTCCCTC GACGAGATCC CGCCGCAGAA CAACAACGTC
                                          PRIMER 2-6
                                            ↓
    1270       1280       1290       1300        1310       1320
CCGCCGAGGC AGGGCTTCGC CCACCGCCTC AGCCCACGTCT CCATGTTCCG CTCCGGCTTC
    1330       1340       1350       1360        1370       1380
AGCAAACAGCA GCGTCAGCAT CATCAGAGCT C CCATGTTCT CGTGGATTCA CCGCTCGGGCG
                                SacI PRIMER 2-7
```

FIG. 8

```
                                        PRIMER 6-1
      1330            1340            1350            1360            1370            1380
AGCAAACAGCA     GCGTCAGCAT     CATCAGAGCT     CCCATGTTCT     CGTGGATTCA     CCGCTCGGGCG
                                        SacI
                                                        PRIMER 6-2
      1390            1400            1410            1420            1430            1440
GAGTTCAACA      ACATCATCCC     CTCGTCACAG     ATCACGCAGA     TCCCCCTGAC     AAAGAGTACG
                                                                    PRIMER 6-3
      1450            1460            1470            1480            1490            1500
AACCTGGGGT      CGGGAACATC     GGTGGTGAAG     GGGCCCCGGAT    TCACGGGGGG     AGACATCCTG
      1510            1520            1530            1540            1550            1560
CGCCGCACTT      CGCCCCGGGCA    GATTTCAACG     CTGCGCGTGA     ACATCACGGC     GCCCCTGTCG
      1570            1580            1590            1600            1610            1620
CAGCGCTATC      GGGTGCGCAT     TCGCTACGCG     TCTACGACAA     ACCTTCAGTT     CCACACGTCA
      1630            1640            1650            1660            1670            1680
ATCGACGGGC      GCCCCATCAA     CCAGGGGAAC     TTCTCGGCGA     CAATGTCGTC     GGGGTCGAAC
      PRIMER 6-4
      1690            1700            1710            1720            1730            1740
CTTCAGTCGG      GAAGCTTCAG     GACCGTCGGGC    TTCACCACCC    CGTTTCAACTT    CTCCAACGGC
                HindIII    PRIMER 6-5
```

FIG. 10

```
              EcoRI SphI EcoT22I EcoRI EcoT14I ScaI SacI HindIII BclI KpnI HindIII
LIGATE TO
EcoRI SITE - AATT-GCATGC-ATGCAT-GAATTC-CCTAGG-AGTACT-GAGCTC-AAGCTT-TGATCA-GGTACC   - LIGATE TO
           - CGTACG-TACGTA-CTTAAG-GGATCC-TCATGA-CTCGAG-TTCGAA-ACTAGT-CCATGG-TCGA  -  HindIII SITE pMCSA8 ──→ pUC18    Amp'
    pMCSK8 ──→ pHSG298  Km'
    pMCSC8 ──→ pHSG398  Cm'
```

| Codon | AA | Count | % | Codon | AA | Count | % | Codon | AA | Count | % |
|---|---|---|---|---|---|---|---|---|---|---|---|
| TTT | Phe | 46 | 0.99% | TCT | Ser | 47 | 1.01% | TAT | Tyr | 33 | 0.71% | TGT | Cys | 20 | 0.43% |

Actually 

| Codon | AA | Count (%) | Codon | AA | Count (%) | Codon | AA | Count (%) | Codon | AA | Count (%) |
|---|---|---|---|---|---|---|---|---|---|---|---|
| TTT | Phe | 46 (0.99%) | TCT | Ser | 47 (1.01%) | TAT | Tyr | 33 (0.71%) | TGT | Cys | 20 (0.43%) |
| TTC | Phe | 132 (2.83%) | TCC | Ser | 59 (1.27%) | TAC | Tyr | 116 (2.49%) | TGC | Cys | 48 (1.03%) |
| TTA | Leu | 18 (0.39%) | TCA | Ser | 33 (0.71%) | TAA | *** | 0 (.00%) | TGA | *** | 0 (.00%) |
| TTG | Leu | 53 (1.14%) | TCG | Ser | 52 (1.11%) | TAG | *** | 0 (.00%) | TGG | Trp | 83 (1.78%) |
| CTT | Leu | 65 (1.39%) | CCT | Pro | 58 (1.24%) | CAT | His | 33 (0.71%) | CGT | Arg | 24 (0.51%) |
| CTC | Leu | 139 (2.98%) | CCC | Pro | 64 (1.37%) | CAC | His | 74 (1.59%) | CGC | Arg | 73 (1.57%) |
| CTA | Leu | 31 (0.66%) | CCA | Pro | 56 (1.20%) | CAA | Gln | 89 (1.91%) | CGA | Arg | 10 (0.21%) |
| CTG | Leu | 86 (1.84%) | CCG | Pro | 79 (1.69%) | CAG | Gln | 133 (2.85%) | CGG | Arg | 42 (0.90%) |
| ATT | Ile | 50 (1.07%) | ACT | Thr | 31 (0.66%) | AAT | Asn | 56 (1.20%) | AGT | Ser | 32 (0.69%) |
| ATC | Ile | 147 (3.15%) | ACC | Thr | 114 (2.44%) | AAC | Asn | 139 (2.98%) | AGC | Ser | 79 (1.70%) |
| ATA | Ile | 32 (0.69%) | ACA | Thr | 35 (0.75%) | AAA | Lys | 38 (0.81%) | AGA | Arg | 37 (0.79%) |
| ATG | Met | 117 (2.51%) | ACG | Thr | 38 (0.81%) | AAG | Lys | 197 (4.22%) | AGG | Arg | 60 (1.29%) |
| GTT | Val | 63 (1.35%) | GCT | Ala | 95 (2.04%) | GAT | Asp | 91 (1.95%) | GGT | Gly | 63 (1.35%) |
| GTC | Val | 138 (2.96%) | GCC | Ala | 148 (3.17%) | GAC | Asp | 155 (3.32%) | GGC | Gly | 212 (4.55%) |
| GTA | Val | 28 (0.60%) | GCA | Ala | 68 (1.46%) | GAA | Glu | 61 (1.31%) | GGA | Gly | 68 (1.46%) |
| GTG | Val | 95 (2.04%) | GCG | Ala | 98 (2.10%) | GAG | Glu | 205 (4.40%) | GGG | Gly | 78 (1.67%) |

| | | | | | | |
|---|---|---|---|---|---|---|
| TTT-Phe | 8 ( .37%) | TCT-Ser | 14 ( .64%) | TAT-Tyr | 6 ( .27%) | TGT-Cys | 4 ( .18%) |
| TTC-Phe | 64 ( 2.93%) | TCC-Ser | 32 ( 1.47%) | TAC-Tyr | 66 ( 3.02%) | TGC-Cys | 21 ( .96%) |
| TTA-Leu | 2 ( .09%) | TCA-Ser | 12 ( .55%) | TAA-*** | 0 ( .00%) | TGA-*** | 0 ( .00%) |
| TTG-Leu | 11 ( .50%) | TCG-Ser | 24 ( 1.10%) | TAG-*** | 0 ( .00%) | TGG-Trp | 48 ( 2.20%) |
| CTT-Leu | 16 ( .73%) | CCT-Pro | 18 ( .82%) | CAT-His | 7 ( .32%) | CGT-Arg | 13 ( .60%) |
| CTC-Leu | 78 ( 3.57%) | CCC-Pro | 44 ( 2.02%) | CAC-His | 42 ( 1.92%) | CGC-Arg | 52 ( 2.38%) |
| CTA-Leu | 5 ( .23%) | CCA-Pro | 21 ( .96%) | CAA-Gln | 11 ( .50%) | CGA-Arg | 3 ( .14%) |
| CTG-Leu | 36 ( 1.65%) | CCG-Pro | 50 ( 2.29%) | CAG-Gln | 64 ( 2.93%) | CGG-Arg | 20 ( .92%) |
| ATT-Ile | 20 ( .92%) | ACT-Thr | 7 ( .32%) | AAT-Asn | 8 ( .37%) | AGT-Ser | 10 ( .46%) |
| ATC-Ile | 88 ( 4.03%) | ACC-Thr | 81 ( 3.71%) | AAC-Asn | 69 ( 3.16%) | AGC-Ser | 46 ( 2.11%) |
| ATA-Ile | 10 ( .46%) | ACA-Thr | 12 ( .55%) | AAA-Lys | 10 ( .46%) | AGA-Arg | 7 ( .32%) |
| ATG-Met | 55 ( 2.52%) | ACG-Thr | 23 ( 1.05%) | AAG-Lys | 107 ( 4.90%) | AGG-Arg | 26 ( 1.19%) |
| GTT-Val | 14 ( .64%) | GCT-Ala | 31 ( 1.42%) | GAT-Asp | 28 ( 1.28%) | GGT-Gly | 23 ( 1.05%) |
| GTC-Val | 70 ( 3.21%) | GCC-Ala | 87 ( 3.99%) | GAC-Asp | 88 ( 4.03%) | GGC-Gly | 134 ( 6.14%) |
| GTA-Val | 5 ( 0.23%) | GCA-Ala | 14 ( .64%) | GAA-Glu | 18 ( .82%) | GGA-Gly | 40 ( 1.83%) |
| GTG-Val | 47 ( 2.15%) | GCG-Ala | 62 ( 2.84%) | GAG-Glu | 112 ( 5.13%) | GGG-Gly | 38 ( 1.74%) |

FIG. 18

| | | | | | | |
|---|---|---|---|---|---|---|
| TTT-Phe | 4 ( .55%) | TCT-Ser | 4 ( .55%) | TAT-Tyr | 1 ( .14%) | TGT-Cys | 2 ( .28%) |
| TTC-Phe | 36 ( 4.97%) | TCC-Ser | 27 ( 3.73%) | TAC-Tyr | 26 ( 3.59%) | TGC-Cys | 2 ( .28%) |
| TTA-Leu | 4 ( .55%) | TCA-Ser | 3 ( .41%) | TAA-*** | 0 ( .00%) | TGA-*** | 0 ( .00%) |
| TTG-Leu | 4 ( .55%) | TCG-Ser | 12 ( 1.66%) | TAG-*** | 0 ( .00%) | TGG-Trp | 10 ( 1.38%) |
| CTT-Leu | 5 ( .69%) | CCT-Pro | 1 ( .14%) | CAT-His | 3 ( .41%) | CGT-Arg | 1 ( .14%) |
| CTC-Leu | 38 ( 5.25%) | CCC-Pro | 9 ( 1.24%) | CAC-His | 10 ( 1.38%) | CGC-Arg | 19 ( 2.62%) |
| CTA-Leu | 3 ( .41%) | CCA-Pro | 1 ( .14%) | CAA-Gln | 8 ( 1.10%) | CGA-Arg | 1 ( .14%) |
| CTG-Leu | 8 ( 1.10%) | CCG-Pro | 23 ( 3.18%) | CAG-Gln | 29 ( 4.01%) | CGG-Arg | 2 ( .28%) |
| ATT-Ile | 8 ( 1.10%) | ACT-Thr | 2 ( .28%) | AAT-Asn | 5 ( .69%) | AGT-Ser | 2 ( .28%) |
| ATC-Ile | 39 ( 5.39%) | ACC-Thr | 32 ( 4.42%) | AAC-Asn | 47 ( 6.49%) | AGC-Ser | 22 ( 3.04%) |
| ATA-Ile | 3 ( .41%) | ACA-Thr | 4 ( .55%) | AAA-Lys | 5 ( .69%) | AGA-Arg | 5 ( .69%) |
| ATG-Met | 9 ( 1.24%) | ACG-Thr | 10 ( 1.38%) | AAG-Lys | 6 ( .83%) | AGG-Arg | 22 ( 3.04%) |
| GTT-Val | 3 ( .41%) | GCT-Ala | 2 ( .28%) | GAT-Asp | 8 ( 1.10%) | GGT-Gly | 2 ( .28%) |
| GTC-Val | 34 ( 4.70%) | GCC-Ala | 26 ( 3.59%) | GAC-Asp | 26 ( 3.59%) | GGC-Gly | 35 ( 4.83%) |
| GTA-Val | 3 ( .41%) | GCA-Ala | 1 ( .14%) | GAA-Glu | 8 ( 1.10%) | GGA-Gly | 8 ( 1.10%) |
| GTG-Val | 6 ( .83%) | GCG-Ala | 6 ( .83%) | GAG-Glu | 31 ( 4.28%) | GGG-Gly | 8 ( 1.10%) |

FIG. 21A

|  | Rice (%) | Rice-leaf(%) | BTHSyn. (%) | BTHNat. (%) |
|---|---|---|---|---|
| Arg-CGC | 29.7 | 43.0 | 38.0 | 4.0 |
| AGG | 24.4 | 21.5 | 44.0 | 14.0 |
| CGG | 17.1 | 16.5 | 4.0 | 4.0 |
| CGT | 9.8 | 10.7 | 2.0 | 14.0 |
| AGA | 15.0 | 5.8 | 10.0 | 52.0 |
| CGA | 4.1 | 2.5 | 2.0 | 12.0 |
| Leu-CTC | 35.5 | 52.7 | 61.3 | 0.0 |
| CTG | 21.9 | 24.3 | 12.9 | 4.8 |
| CTT | 16.6 | 10.8 | 8.1 | 22.6 |
| TTG | 13.5 | 7.4 | 6.5 | 11.3 |
| CTA | 7.9 | 3.4 | 4.8 | 16.1 |
| TTA | 4.6 | 1.4 | 6.5 | 45.2 |
| Ser-AGC | 26.2 | 33.3 | 31.4 | 5.7 |
| TCG | 19.5 | 23.2 | 38.6 | 12.9 |
| TCG | 17.2 | 17.4 | 17.1 | 7.1 |
| TCT | 15.6 | 10.2 | 5.7 | 18.6 |
| TCA | 10.9 | 8.7 | 4.3 | 25.7 |
| AGT | 10.6 | 7.2 | 2.9 | 30.0 |
| Ala-GCC | 36.2 | 44.8 | 74.3 | 8.6 |
| GCG | 24.0 | 32.0 | 17.1 | 8.6 |
| GCT | 23.2 | 16.0 | 5.7 | 48.6 |
| GCA | 16.6 | 7.2 | 2.9 | 34.2 |
| Gly-GGC | 50.4 | 57.0 | 66.0 | 18.9 |
| GGA | 16.2 | 17.0 | 15.1 | 49.1 |
| GGG | 18.4 | 16.2 | 15.1 | 16.9 |
| GGT | 15.0 | 9.8 | 3.8 | 15.1 |
| Pro-CCG | 30.7 | 37.6 | 67.6 | 17.7 |
| CCC | 24.9 | 33.1 | 26.5 | 5.9 |
| CCA | 21.8 | 15.8 | 2.9 | 38.2 |
| CCT | 22.6 | 13.5 | 2.9 | 38.2 |
| Thr-ACC | 52.3 | 65.8 | 66.7 | 16.7 |
| ACG | 17.4 | 18.7 | 20.8 | 18.7 |
| ACA | 16.1 | 9.8 | 8.3 | 29.2 |
| ACT | 14.2 | 5.7 | 4.2 | 35.4 |
| Val-GTC | 42.6 | 51.5 | 73.9 | 6.5 |
| GTG | 29.3 | 34.5 | 13.1 | 13.0 |
| GTT | 19.4 | 10.3 | 6.5 | 40.0 |
| GTA | 8.6 | 3.7 | 6.5 | 43.5 |

|  | Rice (%) | Rice-leaf(%) | BTHSyn. (%) | BTHNat. (%) |
|---|---|---|---|---|
| Ile-ATC | 64.2 | 74.6 | 78.0 | 16.0 |
| ATT | 21.8 | 16.9 | 16.0 | 50.0 |
| ATA | 14.0 | 8.5 | 6.0 | 34.0 |
| Asn-AAC | 71.3 | 89.6 | 90.4 | 25.0 |
| AAT | 28.7 | 10.4 | 9.6 | 75.0 |
| Asp-GAC | 60.0 | 75.9 | 76.5 | 17.6 |
| GAT | 40.0 | 24.1 | 23.5 | 82.4 |
| Cys-TGC | 70.6 | 84.0 | 50.0 | 25.0 |
| TGT | 29.4 | 16.0 | 50.0 | 75.0 |
| Gln-CAG | 59.9 | 85.3 | 78.4 | 18.9 |
| CAA | 40.1 | 14.7 | 21.6 | 81.1 |
| Glu-GAG | 77.1 | 86.2 | 79.5 | 23.1 |
| GAA | 22.9 | 13.8 | 20.5 | 76.9 |
| His-CAC | 69.2 | 85.7 | 76.9 | 0.0 |
| CAT | 30.8 | 14.3 | 23.1 | 100.0 |
| Lys-AAG | 83.8 | 91.5 | 54.5 | 18.2 |
| AAA | 16.2 | 8.5 | 45.5 | 81.8 |
| Phe-TTC | 74.2 | 88.9 | 90.0 | 20.0 |
| TTT | 25.8 | 11.1 | 10.0 | 80.0 |
| Tyr-TAC | 77.9 | 91.7 | 96.3 | 22.2 |
| TAT | 22.1 | 8.3 | 3.7 | 77.8 |

FIG. 21B

| XXC/G% | Rice | Rice-leaf | BTHSyn. | BTHNat. |
|---|---|---|---|---|
| Arg | 71.2 | 81 | 86 | 22 |
| Leu | 70.9 | 84.4 | 80.7 | 16.1 |
| Ser | 62.9 | 73.9 | 87.1 | 25.7 |
| Ala | 60.2 | 76.8 | 91.4 | 17.2 |
| Gly | 68.8 | 73.2 | 81.1 | 35.8 |
| Pro | 55.6 | 70.7 | 94.1 | 23.6 |
| Thr | 69.7 | 84.5 | 87.5 | 35.4 |
| Val | 71.9 | 86 | 87 | 19.5 |
| Ile | 64.2 | 74.6 | 78 | 16 |
| Asn | 71.3 | 89.6 | 90.4 | 25 |
| Asp | 60 | 75.9 | 76.5 | 17.6 |
| Cys | 70.6 | 84 | 50 | 25 |
| Gln | 59.9 | 85.3 | 78.4 | 18.9 |
| Glu | 77.1 | 86.2 | 79.5 | 23.1 |
| His | 69.2 | 85.7 | 76.9 | 0 |
| Lys | 83.8 | 91.5 | 54.5 | 18.2 |
| Phe | 74.2 | 88.9 | 90 | 20 |
| Tyr | 77.9 | 91.7 | 96.3 | 22.2 |

*FIG. 22*

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 2172 base pairs
        ( B ) TYPE: nucleic acid
        ( C ) STRANDEDNESS: double
        ( D ) TOPOLOGY: linear ( i i ) MOLECULE TYPE: other nucleic acid ( i x ) FEATURE:
        ( A ) NAME/KEY: peptide
        ( B ) LOCATION: 1 to 2172
        ( C ) IDENTIFICATION METHOD: E or S
        ( D ) OTHER INFORMATION:

( x i ) SEQUENCE DESCRIPTION: SEQ ID NO:1:

```
ATG GAC AAC AAC CCC AAC ATC AAC GAA TGC ATC CCG TAC AAC TGC CTC     48
Met Asp Asn Asn Pro Asn Ile Asn Glu Cys Ile Pro Tyr Asn Cys Leu
 1               5                  10                  15

AGC AAC CCG GAG GTC GAG GTC CTC GGC GGC GAG AGG ATC GAG ACT GGC     96
Ser Asn Pro Glu Val Glu Val Leu Gly Gly Glu Arg Ile Glu Thr Gly
            20                  25                  30

TAC ACC CCG ATC GAC ATC TCC CTC TCC CTC ACC CAG TTC CTC CTC AGC    144
Tyr Thr Pro Ile Asp Ile Ser Leu Ser Leu Thr Gln Phe Leu Leu Ser
        35                  40                  45

GAG TTC GTC CCG GGC GCC GGC TTC GTC CTC GGA CTA GTT GAT ATA ATA    192
Glu Phe Val Pro Gly Ala Gly Phe Val Leu Gly Leu Val Asp Ile Ile
    50                  55                  60

TGG GGA ATT TTT GGT CCC TCT CAA TGG GAC GCA TTT CTT GTA CAA ATT    240
Trp Gly Ile Phe Gly Pro Ser Gln Trp Asp Ala Phe Leu Val Gln Ile
 65                  70                  75                  80

GAA CAG TTA ATT AAC CAA AGA ATA GAA GAA TTC GCC CGC AAC CAG GCC    288
Glu Gln Leu Ile Asn Gln Arg Ile Glu Glu Phe Ala Arg Asn Gln Ala
                 85                  90                  95

ATC TCC AGG CTC GAG GGC CTC AGC AAC CTC TAC CAG ATC TAC GCC GAG    336
Ile Ser Arg Leu Glu Gly Leu Ser Asn Leu Tyr Gln Ile Tyr Ala Glu
            100                 105                 110

TCC TTC AGG GAG TGG GAG GCC GAC CCG ACC AAC CCG GCC CTC AGG GAG    384
Ser Phe Arg Glu Trp Glu Ala Asp Pro Thr Asn Pro Ala Leu Arg Glu
            115                 120                 125
```

| | | | | | | | | | | | | | | | | |
|---|---|---|---|---|---|---|---|---|---|---|---|---|---|---|---|---|
| GAG | ATG | CGC | ATC | CAG | TTC | AAC | GAC | ATG | AAC | AGC | GCC | CTC | ACC | ACC | GCC | 432 |
| Glu | Met | Arg | Ile | Gln | Phe | Asn | Asp | Met | Asn | Ser | Ala | Leu | Thr | Thr | Ala | |
| | 130 | | | | 135 | | | | 140 | | | | | | | |
| ATC | CCG | CTC | TTC | GCC | GTC | CAG | AAC | TAC | CAG | GTC | CCG | CTC | CTC | TCC | GTC | 480 |
| Ile | Pro | Leu | Phe | Ala | Val | Gln | Asn | Tyr | Gln | Val | Pro | Leu | Leu | Ser | Val | |
| 145 | | | | | 150 | | | | | 155 | | | | | 160 | |
| TAC | GTC | CAG | GCC | GCC | AAC | CTC | CAC | CTC | TCC | GTC | CTC | AGG | GAC | GTC | TCC | 528 |
| Tyr | Val | Gln | Ala | Ala | Asn | Leu | His | Leu | Ser | Val | Leu | Arg | Asp | Val | Ser | |
| | | | | 165 | | | | | 170 | | | | | 175 | | |
| GTG | TTC | GGC | CAG | AGG | TGG | GGC | TTC | GAC | GCC | GCG | ACC | ATC | AAC | AGC | CGC | 576 |
| Val | Phe | Gly | Gln | Arg | Trp | Gly | Phe | Asp | Ala | Ala | Thr | Ile | Asn | Ser | Arg | |
| | | | 180 | | | | | 185 | | | | | 190 | | | |
| TAC | AAC | GAC | TTG | ACC | AGG | CTC | ATC | GGC | AAC | TAC | ACC | GAC | CAC | GCC | GTC | 624 |
| Tyr | Asn | Asp | Leu | Thr | Arg | Leu | Ile | Gly | Asn | Tyr | Thr | Asp | His | Ala | Val | |
| | | 195 | | | | | 200 | | | | | 205 | | | | |
| CGC | TGG | TAC | AAC | ACC | GGC | CTC | GAG | CGC | GTC | TGG | GGC | CCG | GAC | TCT | AGG | 672 |
| Arg | Trp | Tyr | Asn | Thr | Gly | Leu | Glu | Arg | Val | Trp | Gly | Pro | Asp | Ser | Arg | |
| | 210 | | | | | 215 | | | | | 220 | | | | | |
| GAC | TGG | GTC | AGG | TAC | AAC | CAG | TTC | AGG | AGG | GAG | CTG | ACC | CTC | ACC | GTC | 720 |
| Asp | Trp | Val | Arg | Tyr | Asn | Gln | Phe | Arg | Arg | Glu | Leu | Thr | Leu | Thr | Val | |
| 225 | | | | | 230 | | | | | 235 | | | | | 240 | |
| CTC | GAC | ATC | GTC | GCC | CTC | TTC | TCC | AAC | TAC | GAC | AGC | AGG | ACC | TAC | CCG | 768 |
| Leu | Asp | Ile | Val | Ala | Leu | Phe | Ser | Asn | Tyr | Asp | Ser | Arg | Thr | Tyr | Pro | |
| | | | | 245 | | | | | 250 | | | | | 255 | | |
| ATC | CGC | ACC | GTC | TCC | CAG | CTC | ACC | AGG | GAG | ATC | TAC | ACC | AAC | CCG | GTC | 816 |
| Ile | Arg | Thr | Val | Ser | Gln | Leu | Thr | Arg | Glu | Ile | Tyr | Thr | Asn | Pro | Val | |
| | | | 260 | | | | | 265 | | | | | 270 | | | |
| CTC | GAG | AAC | TTC | GAC | GGC | AGC | TTC | CGC | GGC | TCC | GCC | CAG | GGC | ATC | GAG | 864 |
| Leu | Glu | Asn | Phe | Asp | Gly | Ser | Phe | Arg | Gly | Ser | Ala | Gln | Gly | Ile | Glu | |
| | | 275 | | | | | 280 | | | | | 285 | | | | |
| GGC | AGC | ATC | AGG | AGC | CCG | CAC | CTC | ATG | GAC | ATC | CTC | AAC | AGC | ATC | ACC | 912 |
| Gly | Ser | Ile | Arg | Ser | Pro | His | Leu | Met | Asp | Ile | Leu | Asn | Ser | Ile | Thr | |
| | 290 | | | | | 295 | | | | | 300 | | | | | |
| ATC | TAC | ACC | GAC | GCC | CAC | AGG | GGC | GAG | TAC | TAC | TGG | TCC | GGC | CAC | CAG | 960 |
| Ile | Tyr | Thr | Asp | Ala | His | Arg | Gly | Glu | Tyr | Tyr | Trp | Ser | Gly | His | Gln | |
| 305 | | | | | 310 | | | | | 315 | | | | | 320 | |
| ATC | ATG | GCC | TCC | CCG | GTC | GGC | TTC | TCC | GGC | CCG | GAG | TTC | ACC | TTC | CCG | 1008 |
| Ile | Met | Ala | Ser | Pro | Val | Gly | Phe | Ser | Gly | Pro | Glu | Phe | Thr | Phe | Pro | |
| | | | | 325 | | | | | 330 | | | | | 335 | | |
| CTC | TAC | GGC | ACG | ATG | GGC | AAC | GCC | GCC | CCG | CAG | CAA | CGC | ATC | GTC | GCC | 1056 |
| Leu | Tyr | Gly | Thr | Met | Gly | Asn | Ala | Ala | Pro | Gln | Gln | Arg | Ile | Val | Ala | |
| | | | 340 | | | | | 345 | | | | | 350 | | | |
| CAG | CTC | GGC | CAG | GGC | GTC | TAC | AGG | ACC | CTC | AGC | TCC | ACC | CTC | TAC | AGG | 1104 |
| Gln | Leu | Gly | Gln | Gly | Val | Tyr | Arg | Thr | Leu | Ser | Ser | Thr | Leu | Tyr | Arg | |
| | | | 355 | | | | | 360 | | | | | 365 | | | |
| AGG | CCT | TTC | AAC | ATC | GGC | ATC | AAC | AAC | CAG | CAG | CTC | TCC | GTC | CTC | GAC | 1152 |
| Arg | Pro | Phe | Asn | Ile | Gly | Ile | Asn | Asn | Gln | Gln | Leu | Ser | Val | Leu | Asp | |
| | 370 | | | | | 375 | | | | | 380 | | | | | |
| GGC | ACC | GAG | TTC | GCC | TAC | GGC | ACC | TCC | TCC | AAC | TTG | CCG | TCC | GCC | GTC | 1200 |
| Gly | Thr | Glu | Phe | Ala | Tyr | Gly | Thr | Ser | Ser | Asn | Leu | Pro | Ser | Ala | Val | |
| 385 | | | | | 390 | | | | | 395 | | | | | 400 | |
| TAC | AGG | AAG | AGC | GGC | ACC | GTG | GAC | TCC | CTC | GAC | GAG | ATC | CCG | CCG | CAG | 1248 |
| Tyr | Arg | Lys | Ser | Gly | Thr | Val | Asp | Ser | Leu | Asp | Glu | Ile | Pro | Pro | Gln | |
| | | | | 405 | | | | | 410 | | | | | 415 | | |
| AAC | AAC | AAC | GTC | CCG | CCG | AGG | CAG | GGC | TTC | AGC | CAC | CGC | CTC | AGC | CAC | 1296 |
| Asn | Asn | Asn | Val | Pro | Pro | Arg | Gln | Gly | Phe | Ser | His | Arg | Leu | Ser | His | |
| | | | 420 | | | | | 425 | | | | | 430 | | | |
| GTC | TCC | ATG | TTC | CGC | TCC | GGC | TTC | AGC | AAC | AGC | AGC | GTC | AGC | ATC | ATC | 1344 |
| Val | Ser | Met | Phe | Arg | Ser | Gly | Phe | Ser | Asn | Ser | Ser | Val | Ser | Ile | Ile | |
| | | 435 | | | | | 440 | | | | | 445 | | | | |
| AGA | GCT | CCC | ATG | TTC | TCG | TGG | ATT | CAC | CGC | TCG | GCG | GAG | TTC | AAC | AAC | 1392 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Arg | Ala | Pro | Met | Phe | Ser | Trp | Ile | His | Arg | Ser | Ala | Glu | Phe | Asn | Asn |      |
|     | 450 |     |     |     | 455 |     |     |     |     | 460 |     |     |     |     |     |      |
| ATC | ATC | CCC | TCG | TCA | CAG | ATC | ACG | CAG | ATC | CCC | CTG | ACA | AAG | AGT | ACG | 1440 |
| Ile | Ile | Pro | Ser | Ser | Gln | Ile | Thr | Gln | Ile | Pro | Leu | Thr | Lys | Ser | Thr |      |
| 465 |     |     |     |     | 470 |     |     |     |     | 475 |     |     |     |     | 480 |      |
| AAC | CTG | GGG | TCG | GGA | ACA | TCG | GTG | GTG | AAG | GGG | CCC | GGA | TTC | ACG | GGG | 1488 |
| Asn | Leu | Gly | Ser | Gly | Thr | Ser | Val | Val | Lys | Gly | Pro | Gly | Phe | Thr | Gly |      |
|     |     |     |     | 485 |     |     |     |     | 490 |     |     |     |     | 495 |     |      |
| GGA | GAC | ATC | CTG | CGC | CGC | ACT | TCG | CCC | GGG | CAG | ATT | TCA | ACG | CTG | CGC | 1536 |
| Gly | Asp | Ile | Leu | Arg | Arg | Thr | Ser | Pro | Gly | Gln | Ile | Ser | Thr | Leu | Arg |      |
|     |     | 500 |     |     |     |     | 505 |     |     |     |     | 510 |     |     |     |      |
| GTG | AAC | ATC | ACG | GCG | CCC | CTG | TCG | CAG | CGC | TAT | CGG | GTG | CGC | ATT | CGC | 1584 |
| Val | Asn | Ile | Thr | Ala | Pro | Leu | Ser | Gln | Arg | Tyr | Arg | Val | Arg | Ile | Arg |      |
|     |     | 515 |     |     |     | 520 |     |     |     |     | 525 |     |     |     |     |      |
| TAC | GCG | TCT | ACG | ACA | AAC | CTT | CAG | TTC | CAC | ACG | TCA | ATC | GAC | GGG | CGC | 1632 |
| Tyr | Ala | Ser | Thr | Thr | Asn | Leu | Gln | Phe | His | Thr | Ser | Ile | Asp | Gly | Arg |      |
|     | 530 |     |     |     |     | 535 |     |     |     |     | 540 |     |     |     |     |      |
| CCC | ATC | AAC | CAG | GGG | AAC | TTC | TCG | GCG | ACA | ATG | TCG | TCG | GGG | TCG | AAC | 1680 |
| Pro | Ile | Asn | Gln | Gly | Asn | Phe | Ser | Ala | Thr | Met | Ser | Ser | Gly | Ser | Asn |      |
| 545 |     |     |     |     | 550 |     |     |     |     | 555 |     |     |     |     | 560 |      |
| CTT | CAG | TCG | GGA | AGC | TTC | AGG | ACC | GTC | GGC | TTC | ACC | ACC | CCG | TTC | AAC | 1728 |
| Leu | Gln | Ser | Gly | Ser | Phe | Arg | Thr | Val | Gly | Phe | Thr | Thr | Pro | Phe | Asn |      |
|     |     |     |     | 565 |     |     |     |     | 570 |     |     |     |     | 575 |     |      |
| TTC | TCC | AAC | GGC | TCC | AGC | GTC | TTC | ACC | CTC | AGC | GCT | CAT | GTC | TTC | AAC | 1776 |
| Phe | Ser | Asn | Gly | Ser | Ser | Val | Phe | Thr | Leu | Ser | Ala | His | Val | Phe | Asn |      |
|     |     |     | 580 |     |     |     |     | 585 |     |     |     |     | 590 |     |     |      |
| TCC | GGC | AAC | GAG | GTC | TAC | ATC | GAT | CGC | ATC | GAG | TTC | GTC | CCG | GCC | GAG | 1824 |
| Ser | Gly | Asn | Glu | Val | Tyr | Ile | Asp | Arg | Ile | Glu | Phe | Val | Pro | Ala | Glu |      |
|     |     | 595 |     |     |     | 600 |     |     |     |     | 605 |     |     |     |     |      |
| GTC | ACC | TTC | GAG | GCC | GAG | TAC | GAC | CTC | GAG | AGG | GCC | CAG | AAG | GCC | GTC | 1872 |
| Val | Thr | Phe | Glu | Ala | Glu | Tyr | Asp | Leu | Glu | Arg | Ala | Gln | Lys | Ala | Val |      |
|     | 610 |     |     |     |     | 615 |     |     |     |     | 620 |     |     |     |     |      |
| AAC | GAG | CTG | TTC | ACC | TCC | AGC | AAC | CAG | ATC | GGC | CTC | AAG | ACC | GAC | GTC | 1920 |
| Asn | Glu | Leu | Phe | Thr | Ser | Ser | Asn | Gln | Ile | Gly | Leu | Lys | Thr | Asp | Val |      |
| 625 |     |     |     |     | 630 |     |     |     |     | 635 |     |     |     |     | 640 |      |
| ACC | GAC | TAC | CAC | ATT | GAT | CAA | GTA | TCC | AAT | TTA | GTT | GAG | TGT | TTA | TCT | 1968 |
| Thr | Asp | Tyr | His | Ile | Asp | Gln | Val | Ser | Asn | Leu | Val | Glu | Cys | Leu | Ser |      |
|     |     |     |     | 645 |     |     |     |     | 650 |     |     |     |     | 655 |     |      |
| GAT | GAA | TTT | TGT | CTG | GAT | GAA | AAA | AAA | GAA | TTG | TCC | GAG | AAA | GTC | AAA | 2016 |
| Asp | Glu | Phe | Cys | Leu | Asp | Glu | Lys | Lys | Glu | Leu | Ser | Glu | Lys | Val | Lys |      |
|     |     |     | 660 |     |     |     |     | 665 |     |     |     |     | 670 |     |     |      |
| CAT | GCG | AAG | CGA | CTT | AGT | GAT | GAA | CGG | AAT | TTA | CTT | CAA | GAT | CCA | AAC | 2064 |
| His | Ala | Lys | Arg | Leu | Ser | Asp | Glu | Arg | Asn | Leu | Leu | Gln | Asp | Pro | Asn |      |
|     |     | 675 |     |     |     |     | 680 |     |     |     |     | 685 |     |     |     |      |
| TTT | AGA | GGG | ATC | AAT | AGA | CAA | CTA | GAC | CGT | GGC | TGG | AGA | GGA | AAT | ACG | 2112 |
| Phe | Arg | Gly | Ile | Asn | Arg | Gln | Leu | Asp | Arg | Gly | Trp | Arg | Gly | Asn | Thr |      |
|     | 690 |     |     |     |     | 695 |     |     |     |     | 700 |     |     |     |     |      |
| GAT | ATT | ACC | ATC | CAA | GGA | GGC | CAT | GAC | GTA | TTC | AAA | GAG | AAT | TAC | GTT | 2160 |
| Asp | Ile | Thr | Ile | Gln | Gly | Gly | His | Asp | Val | Phe | Lys | Glu | Asn | Tyr | Val |      |
| 705 |     |     |     |     | 710 |     |     |     |     | 715 |     |     |     |     | 720 |      |
| ACG | CTA | TTG | GGT |     |     |     |     |     |     |     |     |     |     |     |     | 2172 |
| Thr | Leu | Leu | Gly |     |     |     |     |     |     |     |     |     |     |     |     |      |

( 2 ) INFORMATION FOR SEQ ID NO:2:

( i ) SEQUENCE CHARACTERISTICS:
        ( A ) LENGTH: 51 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:2:

TTGGTCGACC CATGGACAAC AACCCCAACA TCAACGAATG CATCCCGTAC A  51

( 2 ) INFORMATION FOR SEQ ID NO:3:

( i ) SEQUENCE CHARACTERISTICS:
        ( A ) LENGTH: 71 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:3:

ACGAATGCAT CCCGTACAAC TGCCTCAGCA ACCCGGAGGT CGAGGTCCTC GGCGGCGAGA  60

GGATCGAGAC T  71

( 2 ) INFORMATION FOR SEQ ID NO:4:

( i ) SEQUENCE CHARACTERISTICS:
        ( A ) LENGTH: 42 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:4:

GATCGAGACT GGCTACACCC CGATCGACAT CTCCCTCTCC CT  42

( 2 ) INFORMATION FOR SEQ ID NO:5:

( i ) SEQUENCE CHARACTERISTICS:
        ( A ) LENGTH: 70 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:5:

TCAACTAGTC CGAGGACGAA GCCGGCGCCC GGGACGAACT CGCTGAGGAG GAACTGGGTG  60

AGGGAGAGGG  70

( 2 ) INFORMATION FOR SEQ ID NO:6:

( i ) SEQUENCE CHARACTERISTICS:
        ( A ) LENGTH: 70 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:6:

GAAGAATTCG CCCGCAACCA GGCCATCTCC AGGCTCGAGG GCCTCAGCAA CCTCTACCAG  60

ATCTACGCCG  70

( 2 ) INFORMATION FOR SEQ ID NO:7:

( i ) SEQUENCE CHARACTERISTICS:
        ( A ) LENGTH: 79 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:7:

```
CTACGCCGAG TCCTTCAGGG AGTGGGAGGC CGACCCGACC AACCCGGCCC TCAGGGAGGA    60

GATGCGCATC CAGTTCAAC                                                 79
```

( 2 ) INFORMATION FOR SEQ ID NO:8:

( i ) SEQUENCE CHARACTERISTICS:
        ( A ) LENGTH: 77 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:8:

```
AGTTCAACGA CATGAACAGC GCCCTCACCA CCGCCATCCC GCTCTTCGCC GTCCAGAACT    60

ACCAGGTCCC GCTCCTC                                                   77
```

( 2 ) INFORMATION FOR SEQ ID NO:9:

( i ) SEQUENCE CHARACTERISTICS:
        ( A ) LENGTH: 77 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:9::

```
CTCTGGCCGA ACACGGAGAC GTCCCTGAGG ACGGAGAGGT GGAGGTTGGC GGCCTGGACG    60

TAGACGGAGA GGAGCGG                                                   77
```

( 2 ) INFORMATION FOR SEQ ID NO:10:

( i ) SEQUENCE CHARACTERISTICS:
        ( A ) LENGTH: 79 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:10:

```
CGGTGTAGTT GCCGATGAGC CTGGTCAAGT CGTTGTAGCG GCTGTTGATG GTCGCGGCGT    60

CGAAGCCCCA CCTCTGGCC                                                 79
```

( 2 ) INFORMATION FOR SEQ ID NO:11:

( i ) SEQUENCE CHARACTERISTICS:
        ( A ) LENGTH: 70 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:11:

```
GTCTCTAGAG TCCGGGCCCC AGACGCGCTC GAGGCCGGTG TTGTACCAGC GGACGGCGTG    60

GTCGGTGTAG                                                           70
```

( 2 ) INFORMATION FOR SEQ ID NO:12:

( i ) SEQUENCE CHARACTERISTICS:
        ( A ) LENGTH: 73 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:12:

GACCCTAGGG ACTGGGTCAG GTACAACCAG TTCAGGAGGG AGCTGACCCT CACCGTCCTC 60

GACATCGTCG CCC 73

( 2 ) INFORMATION FOR SEQ ID NO:13:

( i ) SEQUENCE CHARACTERISTICS:
        ( A ) LENGTH: 79 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:13:

TGTAGATCTC CCTGGTGAGC TGGGAGACGG TGCGGATCGG GTAGGTCCTG CTGTCGTAGT 60

TGGAGAAGAG GGCGACGAT 79

( 2 ) INFORMATION FOR SEQ ID NO:14:

( i ) SEQUENCE CHARACTERISTICS:
        ( A ) LENGTH: 68 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:14:

GAGATCTACA CCAACCCGGT CCTCGAGAAC TTCGACGGCA GCTTCCGCGG CTCCGCCCAG 60

GGCATCGA 68

( 2 ) INFORMATION FOR SEQ ID NO:15:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:15:

GGCATCGAGG GCAGCATCAG GAGCCCGCA 29

( 2 ) INFORMATION FOR SEQ ID NO:16:

( i ) SEQUENCE CHARACTERISTICS:
        ( A ) LENGTH: 70 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:16:

AGTAGTACTC GCCCCTGTGG GCGTCGGTGT AGATGGTGAT GCTGTTGAGG ATGTCCATGA 60

GGTGCGGGCT 70

( 2 ) INFORMATION FOR SEQ ID NO:17:

( i ) SEQUENCE CHARACTERISTICS:
        ( A ) LENGTH: 70 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:17:

GCGAGTACTA CTGGTCCGGC CACCAGATCA TGGCCTCCCC GGTCGGCTTC TCCGGCCCGG 60

AGTTCACCTT 70

( 2 ) INFORMATION FOR SEQ ID NO:18:

( i ) SEQUENCE CHARACTERISTICS:
        ( A ) LENGTH: 54 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:18:

TTCACCTTCC CGCTCTACGG CACGATGGGC AACGCCGCCC CGCAGCAACG CATC 54

( 2 ) INFORMATION FOR SEQ ID NO:19:

( i ) SEQUENCE CHARACTERISTICS:
        ( A ) LENGTH: 71 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:19:

GAAAGGCCTC CTGTAGAGGG TGGAGCTGAG GGTCCTGTAG ACGCCCTGGC CGAGCTGGGC 60

GACGATGCGT T 71

( 2 ) INFORMATION FOR SEQ ID NO:20:

( i ) SEQUENCE CHARACTERISTICS:
        ( A ) LENGTH: 71 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:20:

CAGGAGGCCT TTCAACATCG GCATCAACAA CCAGCAGCTC TCCGTCCTCG ACGGCACCGA 60

GTTCGCCTAC G 71

( 2 ) INFORMATION FOR SEQ ID NO:21:

( i ) SEQUENCE CHARACTERISTICS:
        ( A ) LENGTH: 69 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:21:

CGCCTACGGC ACCTCCTCCA ACTTGCCGTC CGCCGTCTAC AGGAAGAGCG CACCGTGGA 60

CTCCCTCGA 69

( 2 ) INFORMATION FOR SEQ ID NO:22:

( i ) SEQUENCE CHARACTERISTICS:
        ( A ) LENGTH: 69 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:22:

CTGAGGCGGT GGCTGAAGCC CTGCCTCGGC GGGACGTTGT TGTTCTGCGG CGGGATCTCG  60

TCGAGGGAG  69

( 2 ) INFORMATION FOR SEQ ID NO:23:

( i ) SEQUENCE CHARACTERISTICS:
        ( A ) LENGTH: 70 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:23:

TGGGAGCTCT GATGATGCTG ACGCTGCTGT TGCTGAAGCC GGAGCGGAAC ATGGAGACGT  60

GGCTGAGGCG  70

( 2 ) INFORMATION FOR SEQ ID NO:24:

( i ) SEQUENCE CHARACTERISTICS:
        ( A ) LENGTH: 80 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:24:

AGAGCTCCCA TGTTCTCGTG GATTCACCGC TCGGCGGAGT TCAACAACAT CATCCCCTCG  60

TCACAGATCA CGCAGATCCC  80

( 2 ) INFORMATION FOR SEQ ID NO:25:

( i ) SEQUENCE CHARACTERISTICS:
        ( A ) LENGTH: 78 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:25:

CGCAGATCCC CCTGACAAAG AGTACGAACC TGGGGTCGGG AACATCGGTG GTGAAGGGGC  60

CCGGATTCAC GGGGGGAG  78

( 2 ) INFORMATION FOR SEQ ID NO:26:

( i ) SEQUENCE CHARACTERISTICS:
        ( A ) LENGTH: 78 bases
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:26:

ACGGGGGGAG ACATCCTGCG CCGCACTTCG CCCGGGCAGA TTTCAACGCT GCGCGTGAAC  60

ATCACGGCGC CCCTGTCG  78

( 2 ) INFORMATION FOR SEQ ID NO:27:

( i ) SEQUENCE CHARACTERISTICS:
        ( A ) LENGTH: 78 bases ( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:27:

```
CCGTCGATTG ACGTGTGGAA CTGAAGGTTT GTCGTAGACG CGTAGCGAAT GCGCACCCGA    60
TAGCGCTGCG ACAGGGGC                                                  78
```

( 2 ) INFORMATION FOR SEQ ID NO:28:

( i ) SEQUENCE CHARACTERISTICS:
  ( A ) LENGTH: 80 bases
  ( B ) TYPE: nucleic acid
  ( C ) STRANDEDNESS: single
  ( D ) TOPOLOGY: linear ( i i ) MOLECULE TYPE: other nucleic acid ( x i ) SEQUENCE DESCRIPTION: SEQ ID NO:28:

```
GAAGCTTCCC GACTGAAGGT TCGACCCCGA CGACATTGTC GCCGAGAAGT TCCCCTGGTT    60
GATGGGGCGC CCGTCGATTG                                                80
```

( 2 ) INFORMATION FOR SEQ ID NO:29:

( i ) SEQUENCE CHARACTERISTICS:
  ( A ) LENGTH: 63 bases
  ( B ) TYPE: nucleic acid
  ( C ) STRANDEDNESS: single
  ( D ) TOPOLOGY: linear ( i i ) MOLECULE TYPE: other nucleic acid ( x i ) SEQUENCE DESCRIPTION: SEQ ID NO:29:

```
GGGAAGCTTC AGGACCGTCG GCTTCACCAC CCCGTTCAAC TTCTCCAACG GCTCCAGCGT    60
CTT                                                                  63
```

( 2 ) INFORMATION FOR SEQ ID NO:30:

( i ) SEQUENCE CHARACTERISTICS:
  ( A ) LENGTH: 63 bases
  ( B ) TYPE: nucleic acid
  ( C ) STRANDEDNESS: single
  ( D ) TOPOLOGY: linear ( i i ) MOLECULE TYPE: other nucleic acid ( x i ) SEQUENCE DESCRIPTION: SEQ ID NO:30:

```
ATGCGATCGA TGTAGACCTC GTTGCCGGAG TTGAAGACAT GAGCGCTGAG GGTGAAGACG    60
CTG                                                                  63
```

( 2 ) INFORMATION FOR SEQ ID NO:31:

( i ) SEQUENCE CHARACTERISTICS:
  ( A ) LENGTH: 70 bases
  ( B ) TYPE: nucleic acid
  ( C ) STRANDEDNESS: single
  ( D ) TOPOLOGY: linear ( i i ) MOLECULE TYPE: other nucleic acid ( x i ) SEQUENCE DESCRIPTION: SEQ ID NO:31:

```
CATCGATCGC ATCGAGTTCG TCCCGGCCGA GGTCACCTTC GAGGCCGAGT ACGACCTCGA    60
GAGGGCCCAG                                                           70
```

( 2 ) INFORMATION FOR SEQ ID NO:32:

( i ) SEQUENCE CHARACTERISTICS:
     ( A ) LENGTH: 26 bases
     ( B ) TYPE: nucleic acid
     ( C ) STRANDEDNESS: single
     ( D ) TOPOLOGY: linear ( i i ) MOLECULE TYPE: other nucleic acid ( x i ) SEQUENCE DESCRIPTION: SEQ ID NO:32:

GGGCCCAGAA GGCCGTCAAC GAGCTG     26

( 2 ) INFORMATION FOR SEQ ID NO:33:

( i ) SEQUENCE CHARACTERISTICS:
          ( A ) LENGTH: 70 bases
          ( B ) TYPE: nucleic acid
          ( C ) STRANDEDNESS: single
          ( D ) TOPOLOGY: linear ( i i ) MOLECULE TYPE: other nucleic acid ( x i ) SEQUENCE DESCRIPTION: SEQ ID NO:33:

ACTTGATCAA TGTGGTAGTC GGTGACGTCG GTCTTGAGGC CGATCTGGTT GCTGGAGGTG     60

AACAGCTCGT     70

( 2 ) INFORMATION FOR SEQ ID NO:34:

( i ) SEQUENCE CHARACTERISTICS:
          ( A ) LENGTH: 58 bases
          ( B ) TYPE: nucleic acid
          ( C ) STRANDEDNESS: single
          ( D ) TOPOLOGY: linear ( i i ) MOLECULE TYPE: other nucleic acid ( x i ) SEQUENCE DESCRIPTION: SEQ ID NO:34:

AATTGCATGC ATGCATGAAT TCCCTAGGAG TACTGAGCTC AAGCTTTGAT CAGGTACC     58

( 2 ) INFORMATION FOR SEQ ID NO:35:

( i ) SEQUENCE CHARACTERISTICS:
          ( A ) LENGTH: 58 bases
          ( B ) TYPE: nucleic acid
          ( C ) STRANDEDNESS: single
          ( D ) TOPOLOGY: linear ( i i ) MOLECULE TYPE: other nucleic acid ( x i ) SEQUENCE DESCRIPTION: SEQ ID NO:35:

AGCTGGTACC TGATCAAAGC TTGAGCTCAG TACTCCTAGG GAATTCATGC ATGCATGC     58

SYNTHETIC INSECTICIDAL GENE, PLANTS OF THE GENUS ORYZA TRANSFORMED WITH THE GENE, AND PRODUCTION THEREOF

FIELD OF THE INVENTION

This invention relates to a synthetic gene encoding an insecticidal protein, a recombinant gramineous plant transformed with the gene and a method for the production thereof. More particularly, it relates to a synthetic gene encoding an analogue of a crystalline protein (δ-endotoxin) originated from *Bacillus thuringiensis* var. kurstaki HD-1, which is known as an insecticidal bacterium, and a method for the production of insect- and/or pest-resistant gramineous plants, which method comprises transforming a given plant with the synthetic gene and growing the plant in an appropriate medium.

BACKGROUND OF THE INVENTION

Recently, an increasing number of researchers are investigating bacterial pesticides which use an insecticidal bacteria or bacterial product as an active ingredient. For example, *Bacillus thuringiensis* (hereinafter, it may be referred to as *B.t.*) is a gram positive bacterium which is known to produce various toxins such as α-, β- and γ-exotoxin and δ-endotoxin, and is highly toxic to many pests (Angus, T. A., Nature 174: 545, 1954). Among these bacterial toxins, δ-endotoxin produced by *B.t.* during the sporulation period is at the center of interest as a crystalline inclusion protein and is currently being used practically. Various *B.t.* strains are known to produce crystalline proteins having properties suited as an active ingredient for pesticides, such as a narrow host spectrum which makes them highly selective, a harmlessness to animals including human beings, and environmental acceptability. The host spectrum of *B.t.* toxin includes many insects belonging to Lepidoptera, Diptera and Coleoptera. Bacteria of *B.t.* strains are classified into 5 types according to the host spectrum of the crystalline proteins produced by them.

As the result of research on the genetic engineering of such crystalline proteins, the production of insect-resistant plants transformed by a gene encoding a toxic protein has become available. For instance, Vaeck et al.( Nature 328: 33-37, 1987) (Plant Genetic Systems Inc., Belgium) succeeded in the preparation of an insect-resistant tobacco (Nicotiana) by integrating a gene encoding an insecticidal protein originated from *B.t.* into the tobacco genome. According to the report, the expression obtained using about the 5'-half of said gene was more efficient than that obtained using the entire gene.

Fischhoff et al. (Bio/Technology 5: 807-813, 1987, Monsanto Inc.) succeeded in the preparation of a recombinant tomato (Lycopersicon) transformed by a gene encoding an insecticidal protein of *B.t.* These two reports, however, failed to detect the expression product of the transformed gene by Western blotting, suggesting that a sufficient expression is hardly attained by means of naturally-occurring genes.

Regarding the translation of the gene, it is interesting that the extent of translation of a given amino acid varies between tissues. Thus, tRNAs in the albumin of corn (Trysacum), which synthesize aggressively zein, a deposited protein rich in glutamine, leucine and alanine, can participate more in the translation of genes encoding these amino acids compared to tRNAs in the embryo of corn. This means that tRNAs in a particular tissue are constructed in such a manner as to promote an optimum translation of genes encoding the desired protein such as zein which should be expressed highly in said tissue.

Wilbur et al. (Plantphysiol. 92: 1-11, 1990) teach about the difference in codon usage between bacteria and higher plants such as dicotyledonous and monocotyledonous plants. Thus, the codon usages for codons XCG and XUA are 1.8% and 3.2% in dicotyledonous plants and 6.3% and 1.4% in monocotyledonous plants. The combined codon usage for codons XXC and XXG (hereinafter, referred to as the codon XXC/G usage, wherein each of the two Xs is independently selected from the group consisting of A, G, C and T) is 45% in dicotyledon and 73.5% in monocotyledon. It is well established that GC content in genes which can be translated is higher in monocotyledon such as gramineous plants, e.g., rice plant, than in dicotyledon. As to bacterium, the codon usage varies depending on the strains. For instance, the codon usage for codons XGG, XUA, and XXC/G are 10.4%, 3.3% and 24.4%, respectively in the gene encoding δ-endotoxin, one of *B.t.* toxins produced by B.t. var kurstaki HD-1 (cryIA(b)). These facts suggest that tRNAs in plant tissues can hardly afford a sufficient translation of bacterial genes.

Recently, Prederick (Bio/Technology 8: 939-942, 1990) (Monsanto Inc.) reported for the first time that B.t. toxin can be expressed highly in cotton plant (Gossypium) transformed by a modified gene in which the 3'-half is deleted and codons are changed. Thus, a gene encoding *B.t.*-originated δ-endotoxin was chemically synthesized and ligated downstream of the 35S promoter of cauliflower mosaic virus, said promoter containing the enhancer region of the 35S promoter, and the resultant gene was used for the transformation by means of Agrobacterium. The synthetic gene was prepared from genes of *Bacillus thuringiensis* var. kurstaki HD-1 (cryIA(b)) and HD-73 (cryIA(c)). The synthetic gene allowed a high expression of *B.t.* toxin (about 0.05-0.1% of soluble protein in leaves) with an expression rate of about 50-100 times that obtained using a gene encoding native *B.t.* toxin. When insecticidal activity was examined by bioassay using cotton-ball worms, a protection activity on an order of about 70-100% was observed.

Frederic et al. (Proc. Natl. Acad. Sci. USA 88: 3324-3328, 1991) attempted to determine regions on a bacterial gene in which codon modifications would be effective for the expression of said gene in plants. They selected 9 regions to be modified and prepared various genes in which any or all of the 9 regions were modified, and they transformed each of them into tobacco and tomato plants using Agrobacterium. When the expression efficiency obtained by a gene which contains nine modified regions is estimated to be 100%, they found that a gene containing four modified regions within 700 bp from 5'-terminus showed about 80% ,efficiency. On the contrary, no *B.t.* toxin was detected in plants transformed by genes whose 3'-half region was modified. The expression efficiency was highest in the case of a gene containing a modification in the region(s) between 246 to 283 bp from the 5'-terminus, and it was 53-80% of that obtained by a gene containing nine modified regions.

Prior to the present invention, as mentioned above, Monsanto Inc. showed that a high expression of bacterial protein (*B.t.* protein) in plants such as cotton, tobacco, tomato and the like can be achieved through the modification of codon usages. Lubrizol Genetics Inc. disclosed a synthetic gene encoding insecticidal crystalline protein (Japanese Publication (KOKAI) No. 186989/1990), in which the codon usage is discussed. The exemplified plant, however, is merely tobacco.

As is clear from the above, prior to the present invention, expression of bacterial toxin in plants has been reported only in dicotyledonous plants. There have been no reports that show a detectable amount of insecticidal crystalline protein being expressed in monocotyledonous plants.

BRIEF DESCRIPTION OF THE DRAWINGS

FIG. 7: A base sequence of primers (segment 2) used in PCR.

FIG. 8: A base sequence of primers (segment 6) used in PCR.

FIG. 10: Cloning sites used for the replacement at the time of the construction of plasmids pMCSC8, pMCSA8 and pMCSK8.

FIG. 16: A codon usage of genes isolated from rice plant (Oryza).

FIG. 17: A codon usage of genes which appear to be expressed highly in leaves of rice plant.

FIG. 18: A codon usage of a synthetic gene having a base sequence of SEQ ID NO:1.

FIG. 21: An alignment of codon usages for individual amino acids observed in: Oryza gene; genes which appear to be expressed highly in leaves of rice plant; synthetic gene having a base sequence of SEQ ID NO:1; and native genes encoding individual amino acid in $B.t.$ toxin.

FIG. 22: An alignment of codon XXC/G usages for individual amino acids observed in: Oryza gene; genes which appear to be expressed highly in leaves of rice plants; synthetic gene having a base sequence of SEQ ID NO:1; and native genes encoding individual amino acid (except for methionine and tryptophan) in $B.t.$ toxin.

DETAILED DESCRIPTION OF THE INVENTION

Figure 1:
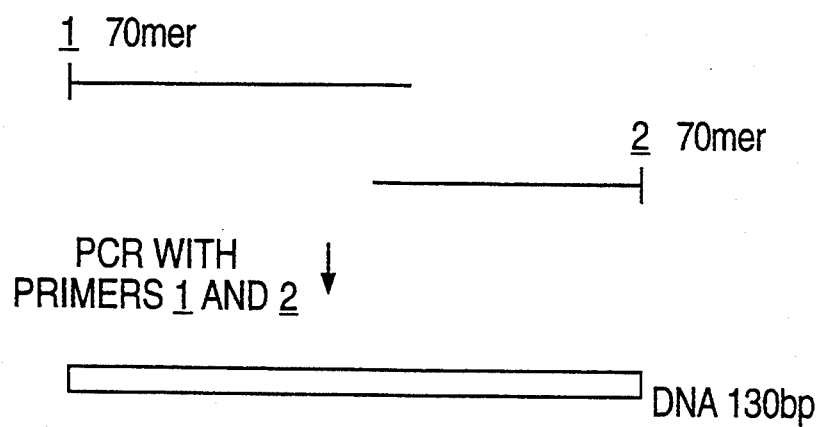
FIG. 1: A schematic description of the synthesis of a double stranded DNA by PCR (polymerase chain reaction).

These facts indicate that it is important for the expression of a $B.t.$ toxin-encoding gene in plants to modify the bacterial gene by deleting its 3'-half and to bring the codon usage in conformity with the genes of the plants. Under the circumstances, the present inventors have investigated extensively and succeeded in the preparation of a synthetic gene encoding an analogue of $B.t.$ toxin which can be expressed highly in gramineous plants for the first time.

Thus, the present invention provides a synthetic gene encoding a bacterial-insecticidal protein, said gene having a base sequence modified to make the codon usage conform to genes of gramineous plants, an expression vector containing said gene, gramineous plants transformed With the vector, and a method for producing the same.

Throughout the specification, the conformity of codon usages between the synthetic gene and the genes of the plants to be transformed are expressed by the proportion (%) of different codon usages.

The present invention is directed to the expression of the synthetic gene in plants belonging to Gramineae such as Oryza, Triticum, Hordeum, Secalu and Eshinochloa, with a preference to Oryza (rice plant).

The synthetic gene of the invention was prepared on the basis of the gene encoding δ-endotoxin originated from Bacillus thuringiensis var. kurstaki HD-1, which may be abbreviated as $B.t.$ The term "recombinant plant" or "transformed plant" refers to a plant carrying the synthetic gene of the invention as the result of the transformation and being resistant to pests.

The term "$B.t.$ toxin" refers to a toxic protein originated from $B.t.$ In the specification, $B.t.$ toxin means not only the naturally-occurring toxic proteins produced by $B.t.$ but also a protein encoded by the synthetic gene of the invention and, when transformed into plants and expressed by them, affording the plant insect-resistant properties.

The terms "native $B.t.$ gene" refers to a naturally-occurring gene which encodes $B.t.$ toxin.

The gene of the present invention was prepared using chemical and enzymatic procedures in such a manner as to encode a protein functionally equivalent to native $B.t.$ toxin. The gene is designed to include insertions of 6 bp restriction sites approximately every 200–400 bp to facilitate further modification(s). These sites make it easy to replace a region such as that responsible for the host-specificity or the like with another. The synthesis of the gene of the invention can be accomplished by changing base components of each codon to those suitable for plants without affecting the amino acid encoded thereby. The modification is done with the intention of fitting the codon usage of a native $B.t.$ gene to those of genes in gramineous plants. The suitable codon usage should be determined taking the following codon usages into consideration.

a) The codon usage of 61 codons from total 64 codons except for three stop codons (TAA, TAG and TGA).
b) The codon usage for each of 18 amino acids from a total 20 amino acids except for methionine and tryptophan which are encoded by merely one codon.
c) The codon XXC/G usage for these 18 amino acids. In this case, the difference between monocotyledonous plants and dicotyledonous plants in codon XXC/G usage should be considered.

When the synthetic gene of the invention is desired to be expressed highly in a particular plant tissue such as a leaf, it is important to bring the codon usage of said synthetic gene in conformity with that of genes which appear to be highly expressed in leaves because optimum codon usage varies between tissues. This can be performed by designing the base sequence of the synthetic gene on the basis of the codon usages a), b) and c) of genes being expressed highly in leaves.

It is also preferable that the codon encoding an individual amino acid be distributed uniformly throughout the synthetic gene.

Restriction sites to be incorporated into the synthetic gene, which serve as the linking sites of DNA segments, are selected from those found in a base sequence predicted from amino acid sequences of native protein of B. t. var kurstaki HD-1 (cryIA(b)) (J. Bac. 166: 801-811, 1986). If the plant to be transformed is rice plant (Oryza), the base sequence is modified considering the codon usages of known genes in various Oryza tissues as determined below.

1) Mean value of codon usages in genes of various tissues of rice plant obtained according to d), e) and f) is determined.
   d) The codon usage of 61 codons from total 64 codons except for three stop codons (FIG. 16);
   e) The codon usage for each of 18 amino acids from a total 20 amino acids except for methionine and tryptophan which are encoded by one codon (FIG. 21, Rice); and
   f) The codon XXC/G usage for these 18 amino acids. (FIG. 22, Rice).
2) Codon usages of genes which appear to be expressed highly in leaves of rice plant are determined as follows.
   g) The codon usage of 61 codons from the total 64 codons except for three stop codons (FIG. 17);
   h) The codon usage for each of 18 amino acids from a total 20 amino acids except for methionine and tryptophan which are encoded by one codon (FIG. 21, Rice-leaf); and
   i) The codon XXC/G usage for the above 18 amino acids (FIG. 22, Rice-leaf).

For the determination of codons, it is recommended to take the following matters in consideration. The base sequence of a gene encoding *B.t.* δ-endotoxin is modified so as to fit the codon usage for each amino acid to that of Oryza gene obtained in d) above (FIG.16) at the rate of about ±4%, more preferably, to that obtained in e) above (FIG. 21, Rice) at the rate of 40%. More preferably the codon usage for amino acids dominant in *B.t.* toxin such as, in this case of cryIA(b), ten amino acids including arginine, leucine, serine, glycine, threonine, valine, isoleucine, asparagine, glutamic acid, and phenylalanine, fits to the codon usage obtained in f) above (FIG. 22, Rice) at the rate of ±25%. The wording "amino acids dominant in *B.t.* toxin" herein used means that the amino acids are ranked in upper positions as to the content in *B.t.* toxin. For purposes of the present invention, it is most preferable to select codons in such a manner as to bring the codon usage as close as possible to those obtained in g) (FIG. 17), h) (FIG. 21, Rice-leaf) and i) (FIG. 22, Rice-leaf).

It is desirable that codons encoding an individual amino acid are distributed uniformly throughout the synthetic gene as previously mentioned.

An illustrative synthetic gene thus designed is shown in SEQ ID NO: 1. FIG. 18 shows the codon usage of 61 codons from 64 codons (excluding stop codons), FIG. 21 (BTHsyn.) shows the codon usage for individual 18 amino acids (excluding methionine and tryptophan), and FIG. 22 (BTHsyn) Shows the codon XXC/G usage for individual 18 amino acids of the synthetic gene of SEQ ID NO:1. A comparison of codon usage concerning 61 codons, excluding stop codons, between the synthetic gene and native genes of rice plant revealed that the difference is about 2% for all codons except for AAC (3.51%) encoding arginine. The codon usage became more agreeable when a comparison was carried out between the synthetic gene and genes which appear to be highly expressed in Oryza leaves. Thus, the difference was highest (3.33%) for AAC encoding asparagine and others were in fairly good agreement, indicating that the codon usage of synthetic gene is suited more closely to that of genes contained in leaves of rice plant.

When the comparison was carried out on the codon usage for individual 18 amino acid from total 20 amino acids excluding methionine and tryptophan, almost all the codon usages were in fairly good agreement with the difference of about 20% except for CCG encoding proline (36.9%). The codon usage became more agreeable when the comparison was carried on genes which appear to be highly expressed in Oryza leaves. Thus, the difference was highest (37%) for AAG encoding lysine and others were in good agreement, indicating that the codon usage of synthetic gene is suited more closely to that of genes contained in leaves of rice plant. The comparison of codon usage was also conducted on codons encoding individual 10 amino acids which are dominant in *B.t.* toxin including arginine, leucine, serine, glycine, threonine, valine, isoleucine, asparagine, glutamic acid, and phenylalanine. A fairly good agreement was observed in all amino acids with a difference of about 15% except for one amino acid (24.2% in serine). The codon XXC/G usage for these amino acids in synthetic gene and that in genes which appear to be expressed highly in Oryza leaves were compared, demonstrating that the former is close to the latter with one exception (13.2% in serine).

As will be easily appreciated by one skilled in the art, DNA encoding the insecticidal protein of the invention can be easily modified by a conventional method such as deletion, replacement or addition of nucleotide(s), resulting in DNA derivatives encoding insecticidal proteins having the same or improved activity. Therefore, the present invention also provides such a modified gene obtained by conventional methods.

Experimental Methods

Preparation of a gene designed as mentioned above can be carried out using any of conventional methods. For example, single stranded oligonucleotides of about 20 to 100 bp are synthesized and each segments are combined by PCR to yield double stranded DNA (Am.

J. Hum. Genet.37: 172, 1989) as shown below and in FIGS. 1-3.

Method A:

This is a basic method which is schematically illustrated in FIG. 1. According to this method, a desired double stranded DNA can be obtained by synthesizing a pair of 70 nt olygonucleotides, each of which has about 10 bp complementary sequence at 3'-terminus, and reacting in a standard reaction mixture for PCR.

Figure 2:
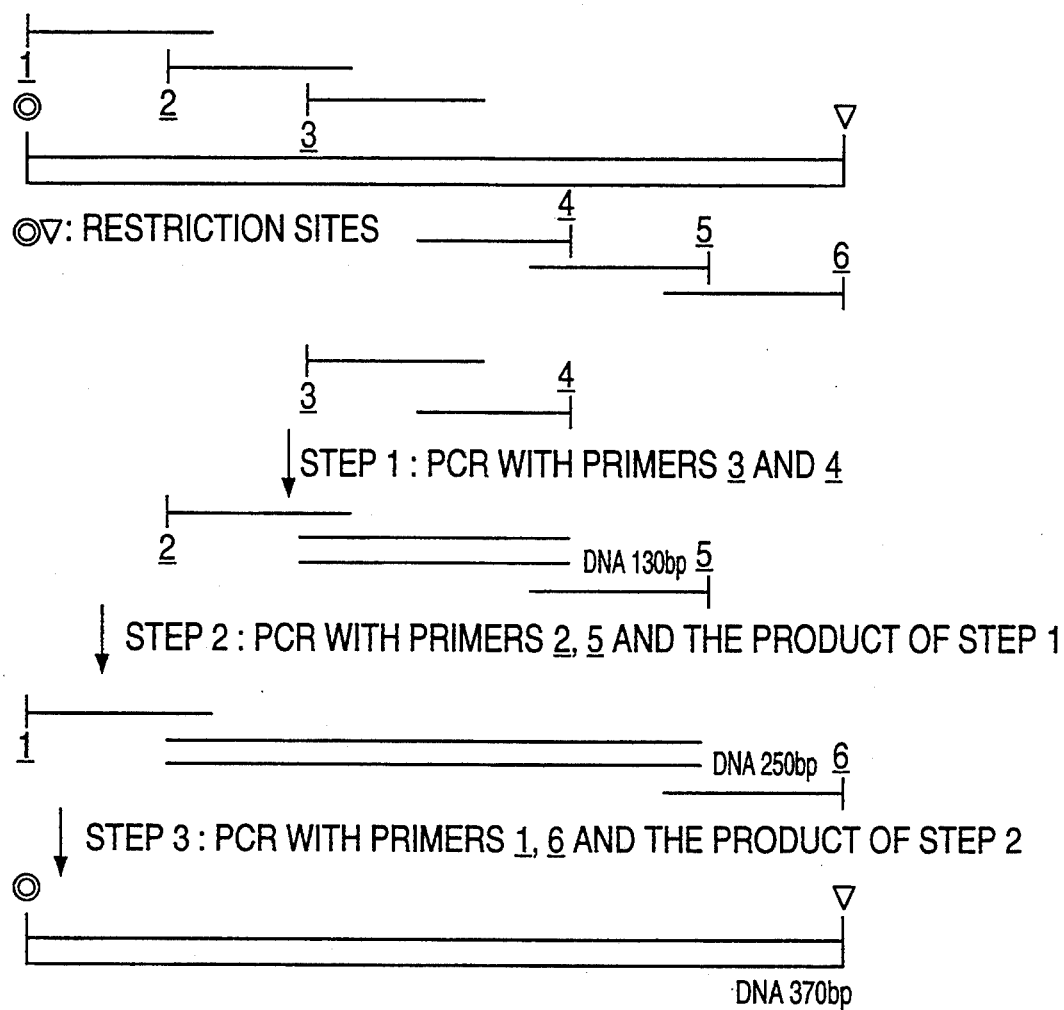
FIG. 2: A schematic description of the synthesis of a double stranded DNA by PCR from oligonucleotide.

Method B:

This is an application of the basic method A which is schematically illustrated in FIG. 2. According to Method B, a 370 bp double stranded DNA can be prepared as follows. Oligonucleotides 3 and 4 are treated in the same manner as Method A above to yield a 130 bp double stranded DNA. The resultant DNA is reacted with oligonucleotides 2 and 5 by PCR, and the resultant DNA, oligonucleotides 1 and 6 are subjected to PCR to yield the desired double stranded DNA. This method has the advantage of that a long double-stranded DNA on which restriction sites exist apart can be easily obtained.

Figure 3:
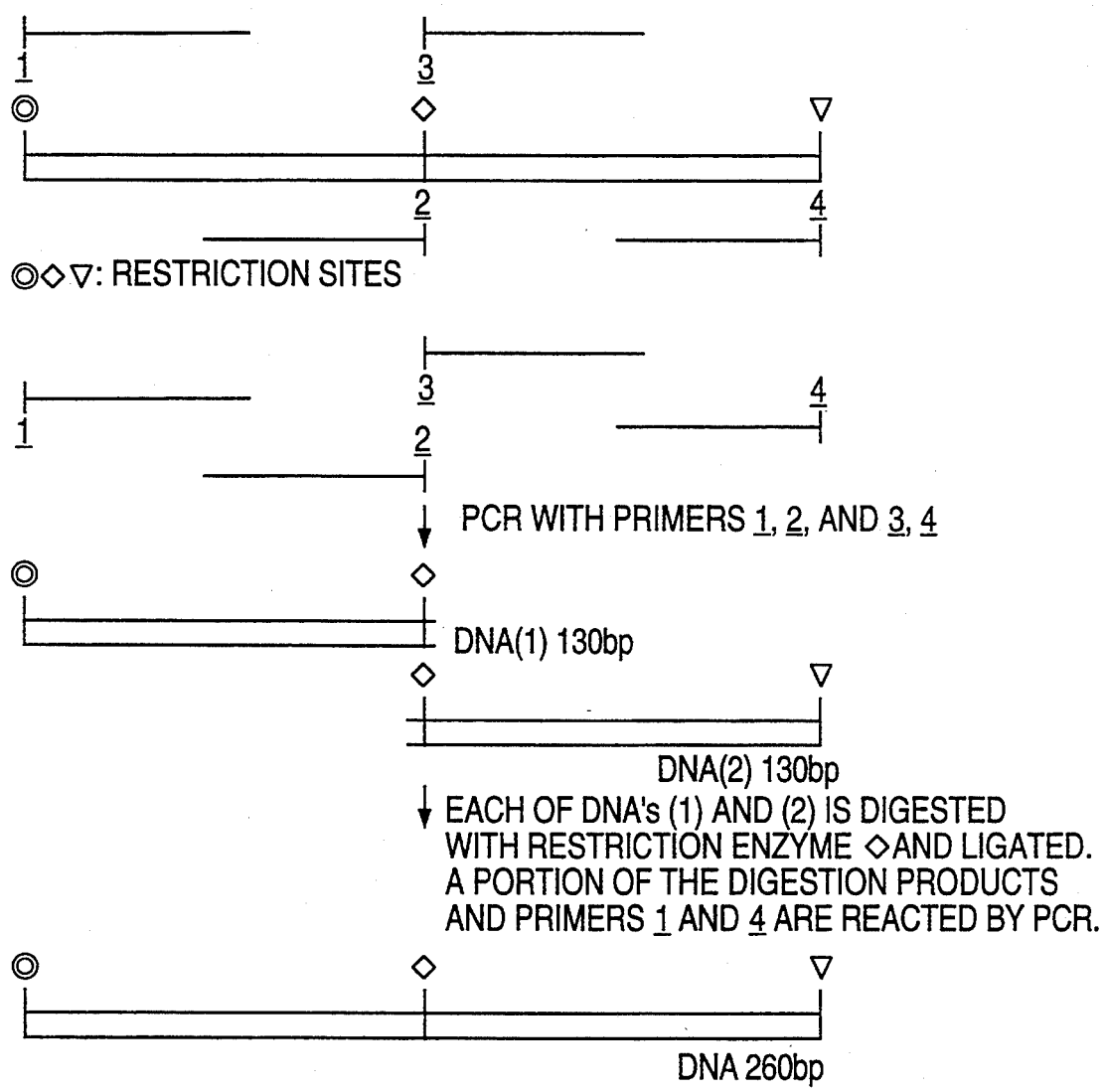
FIG. 3: A schematic description of the synthesis of a double stranded DNA by PCR from oligonucleotide.

Method C:

This is another application of the basic method A which is schematically illustrated in FIG. 3. According to Method C, a 260 bp double stranded DNA which contains restriction sites as shown in FIG. 3 can be prepared as follows. Pairs of oligonucleotides 1 and 2, and 3 and 4 are treated in the same manner as Method A to yield a 130 bp double stranded DNA. The resultant DNA is digested with restriction enzymes corresponding to the restriction sites where the fragments are adjoining, which is followed by the ligation with a ligase. A portion of the products and oligonucleotides 1 and 4 are again subjected to PCR to yield a desired double stranded DNA. This method has the advantage of that the cloning of individual short segment is not required and the amplification of the enzymatically-ligated DNA can be proceeded promptly, thereby facilitating the cloning of the desired DNA.

Although these methods are suited for the preparation of the desired DNA, they are not restrictive and a combined method of Methods B and C is also useful.

Each of the double stranded DNA segments prepared according to the Methods 2 and/or 3 is then cloned into an appropriate cloning vector having multi-cloning sites. Examples of appropriate vectors include those derived from Escherichia coli such as pUC18, 19 (Gene 33: 103, 1985), pHSG298, 299, 398, 399 (Gene 61: 63, 1987), pBSIIKS+/−, pBSIISK+/− (Stratagene Inc.) which are derived from the ColE1 plasmid and analogues thereof which can be obtained by modifying cloning sites of these existing vectors. The sequence of cloned segment can be confirmed by the dideoxy method of Sanger et al. (Proc. Natl. Acad. Sci. 74: 5463-5467, 1977). Individual DNA segment having restriction sites at the both ends is then digested with corresponding restriction enzymes and ligated in the presence of T4 DNA ligase to yield a full length structural gene encoding B.t. toxin.

For the expression of B.t. toxin, the structural gene is inserted into a plasmid vector containing promoter and terminator, and intron, if necessary, suited for the expression of structural gene in gramineous plants.

Promoters can be selected from those known to be functional in plants. Examples of such promoters include a promoter derived from cauliflower mosaic virus such as CaMV35S (pBI221: EMBO. J. 6: 3901–3907, 1987), rbcS (ribulose 1.5-bisphosphate carboxylase), Cab (chlorophyll a/b binding protein)(Science 244: 174, 1989) and the like.

Examples of terminators includes those derived from cauliflower mosaic virus, NOS (nopaline synthetase) gene and the like. Vectors which contain intron(s) between a structural gene and promoter are also useful as high-expression vectors. Examples of introns include the first intron of corn Adh1 (alcohol dehydrogenase gene; Genes & Development 1: 1183–1200, 1987), the first intron of castor-oil plant Cat (catalase gene; Tanaka, et al. Nucleic Acids Research 18: 6767–6770, 1990) and the like.

For purposes of the invention, the expression vector preferably contains two or more foreign genes selected from the group consisting of hygromycin phosphotransferase gene, neomycin phosphotransferase gene, chloramphenicol acetyltransferase gene, β-glucuronidase gene and the like subject to that one of such foreign genes serves as a selective marker which offers a measure for the selection of desired colonies. Hygromycin phosphotransferase gene is a preferred selective marker gene.

A foreign gene encoding a selective marker and others may be contained in the same expression vector or in separate vectors which are used simultaneously at the time of the transformation.

The vector of the present invention is used for the transformation of gramineous plants. The transformation generally comprises the following steps. Protoplasts are prepared from a given gramineous plant and suspended in a liquid medium. The transformation of expression vectors into protoplasts can be carried out conventionally by, for instance, the electric pulse-treatment. The resultant protoplasts are then incubated in a medium containing gramineous cultured cells to obtain colonies. Desired colonies are selected and grown to regenerate a plant as a recombinant product (Shimamoto et al. Nature 337: 274–276, 1989). The procedures will be explained in detail below.

The preparation of protoplasts can be carried out using as a source any of currently existing agricultural species of rice plant such as NIPPONBARE, KOSHIHIKARI, SASANISHIKI and the like. A cell suspension or callus prepared from plant tissues such as matured or unmatured seeds, leaf sheaths and/or roots is cultivated in a liquid medium and treated in a solution containing an enzyme capable of decomposing cell walls such as cellulase, under the condition of 0–50 spm, 25°–30° C. for about 3–16 hr. After the enzymatic treatment, the culture is filtered to separate non-digested substances. To the filtrate is added 2–5 times volume of KMC solution (0.118M potassium chloride, 0.0817M magnesium chloride, 0.085M calcium chloride, pH 6.0) (Theor. Appl. Genet. 53: 57–63, 1978) and the like, and centrifuged to give a purified protoplasts.

Transformation can be carried out, for example, by suspending 1–100 μg/ml of expression vectors carrying the structural gene prepared as mentioned above and (2–10)$\times 10^6$/ml of protoplasts prepared from plants in a liquid medium such as a buffer containing 30–200 mM calcium chloride, 0–50 mM magnesium chloride and 0.2–0.6M mannitol, and impressing electric pulse thereon. Preferably, the electric pulse-treatment is carried out by direct-current pulse using 100–1000 μF condenser (initial voltage, 200–1000 V/cm; and pulse interval, about 1–50 msec) as described in Japanese Publication (KOKAI) No. 181791/1989.

The protoplasts treated with pulse are suspended into a liquid medium such as RS/MS, a mixture of inorganic components of R2 medium (Plant. Cell. Physiol. 14: 1113, 1973) and a solution of vitamin mixture of MS medium (Murashige and Skoog, 15: 473–497, 1962) or MS medium, said medium preferably containing 0.2–0.5% potassium nitrate as nitrogen source. The suspension is mixed with an equal amount of a medium such as R2/MS or MS containing about 1.0–3.0% agarose and spread thinly in a petri dish promptly to solidify it. The final concentration of protoplasts in solid medium is preferably about $(5-50) \times 10^5$/ml.

The solidified agarose is cut into segments of about 5–20 mm large and incubated in the dark with gentle shaking (20–50 rpm) in a liquid medium at 23°–27° C.

When the protoplasts are originated from gramineous plants, the medium preferably contains about 100–300 mgPW/dish of cultured cells of rice plant. Alternatively, the co-cultivation can be carried out using a container, whose bottom is formed or attached by membrane filter. Thus, a liquid medium containing protoplasts is placed in said container, which in turn soaked in a liquid medium containing cultured cells of rice plant in petri dish. The cultured cells are preferably in the form of fine cell masses which are under the active cell-division. Such cultured cells can be easily obtained by subculturing a callus prepared from a tissue of rice plant such as seed, stem, root or anther to a liquid medium repeatedly While selecting cells capable of dividing quickly.

After 3 to 4-week-incubation, 0.5–1 mm colonies appear. If the vector contains a foreign gene which also serves as marker gene, such as hygromycin phosphotransferase gene (hph), selection of desired transformants can be facilitated by adding 10–100 μg/ml hygromycin to medium on 7–20 days after the initiation of the cultivation and continuing the incubation. The selected colony is transferred to a growth medium and incubated with lighting (1000–4000 lux) at 23°–27° C. for 2–4 weeks to obtain a callus of about 3–6 mmϕ. A growth medium may be an agar medium such as R2 medium supplemented by 2 μg/ml of phytohormone such as 2,4-dichlorophenoxyacetic acid (2,4-D) and 0.1–1.0% agarose. Individual callus is isolated. When the vector used for the transformation contains hph gene as one of foreign genes, the isolated callus is grown in the same medium supplemented with 2.0–50 μg/ml hygromycin to confirm the expression of hygromycin resistance.

The callus is grown in R2/MS medium containing 0.5–1.5% agarose, said medium being formalin-free or supplemented with 1–10 mg/l cytokinin, with-lighting (2000–4000 lux) at 23°–27° C. for 2–10 weeks to form an adventitious (indefinite) bud or adventive embryo, which is then subjected to 2 to 3-week-culture in hormone-free R2/MS medium to give a young plant which can be transplanted. The young plant is raised in an appropriate medium such as vermiculite and the like to obtain desired transformed plant, i.e., recombinant rice plant.

The presence of a synthetic gene of the invention in transformed cells or plants can be confirmed by isolating DNA according to a any of known methods, e.g., 10 Mol Gen. Genet. 211: 172, 1988, and subjecting the isolated DNA to PCR (Am. J. Hum. Genet. 37: 172, 1985) or Southern hybridization (J. Mol. Biol. 98: 505, 1980). When the transformed cells express genes integrated into plant genome, the confirmation is effected by Northern hybridization (Thomas, P. et al. Proc. Natl. Acad. Sci. 77: 5201, 1980) using the transformed gene as a probe, or Western blotting (Towbin et al. Proc. Natl. Acad. Sci. 76: 4350, 1979) using antiserum raised against expression product of said transformed gene.

Following Examples further illustrate and detail the invention disclosed, but should not be construed to limit the invention.

EXAMPLE 1

Chemical and Enzymatic Synthesis of Structural Gene Encoding B.t. Toxin and the Construction of an Expression Vector (1) Preparation of Oligodeoxynucleotide Oligonucleotide for each of segments 1–6 for the construction of B.t. toxin-encoding structural gene whose base sequence is shown in SEQ ID NO:1 can be synthesized according to any of known standard methods (Matteucci et al. J. Am. Chem. Soc. 103: 3185–3192, 1981; and Beaucage et al. Tetrahedron lett. 22: 1859–1862, 1981). All the oligonucleotide were prepared using solid phase phosphoramidite-triester coupling method using Applied Biosystems 391 DNA Synthesizer. Oligomers were deprotected and separated from solid carriers conventionally using 28% ammonia water. The crude oligonucleotide mixture was purified according to the methods of Mcbridg et al. (Biotechniques 6: 362–367, 1988) using oligonucleotide purifying cartridge (OPC column, Applied Biosystems).

(2) Preparation of Double Stranded DNA by PCR

Figure 11:
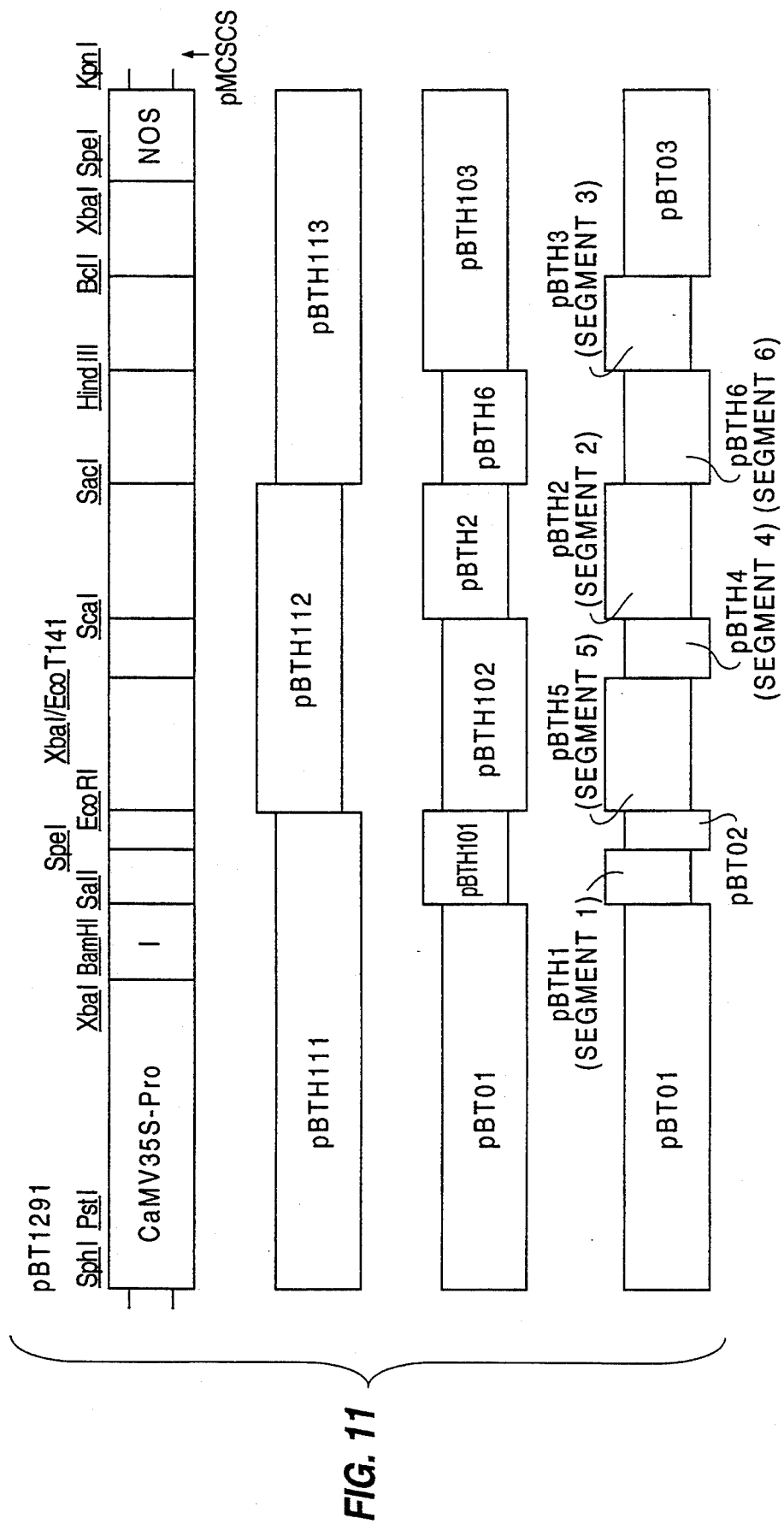
FIG. 11: A schematic description of the construction of plasmid pBT1291.

The length and sequence of oligonucleotide used for the preparation of each segment are shown in FIGS. 4–9 and restriction sites of each segment are shown in FIG. 11. The preparation of each segments was accomplished using Method B or C as explained above.

1) Preparation of Segment 1

Figure 4:
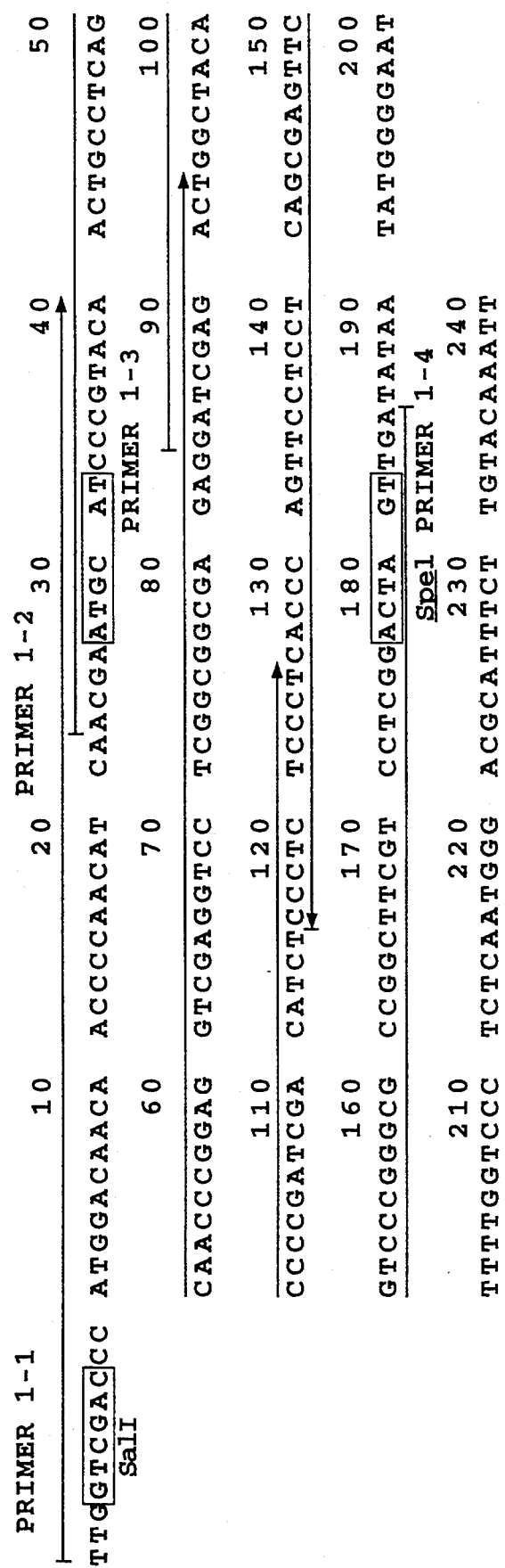
FIG. 4: A base sequence of primers (segment 1) used in PCR.

Segment 1 is a 190 bp fragment having SalI and SpeI sites at either end (FIG. 4). This segment was prepared according to the Method B using 4 oligonucleotide primers. Senseprimer 1-3 and antisenseprimer 1-4 are reacted by PCR (Am. J. Hum. Genet. 37: 172, 1985). PCR was carried out in total 100 μl reaction mixture containing 10 μM each of primers, 10 mM Tris-HCl (pH 8.3), 1.5 mMMgCl$_2$, 50 mM KCl 0.005% Tween 20, 0.005% NP-40, 0.001% Gelatin, 200 μM each of dATP, dGTP, dCTP and dTTP, and 5 units REPLITHERM Thermostable DNA Polymerase (EPISENTRE Inc.) in DNA Thermal Cycler PJ1000 (PERKIN-ELMER CETUS Inc.). The reaction was carried out by repeating 30 times of reaction cycles which comprises: at 94° C., 1 min, 50°–55° C., 2 min, and 72° C., 3 min. PCR for the preparation of double stranded DNA in Method B are generally carried out under the same conditions except that primers and DNA are changed. Another PCR was conducted using 5 μl of the resultant PCR mixture containing 102 bp DNA, senseprimer 1-2 and antisenseprimer 1-4 under the same conditions to yield a 163 bp DNA. Another PCR was carried out using 5 μl of the reaction mixture, senseprimer 1-1 and antisenseprimer 1-4 to yield the desired 196 bp double stranded DNA.

2) Preparation. of Segment 5

Figure 5:
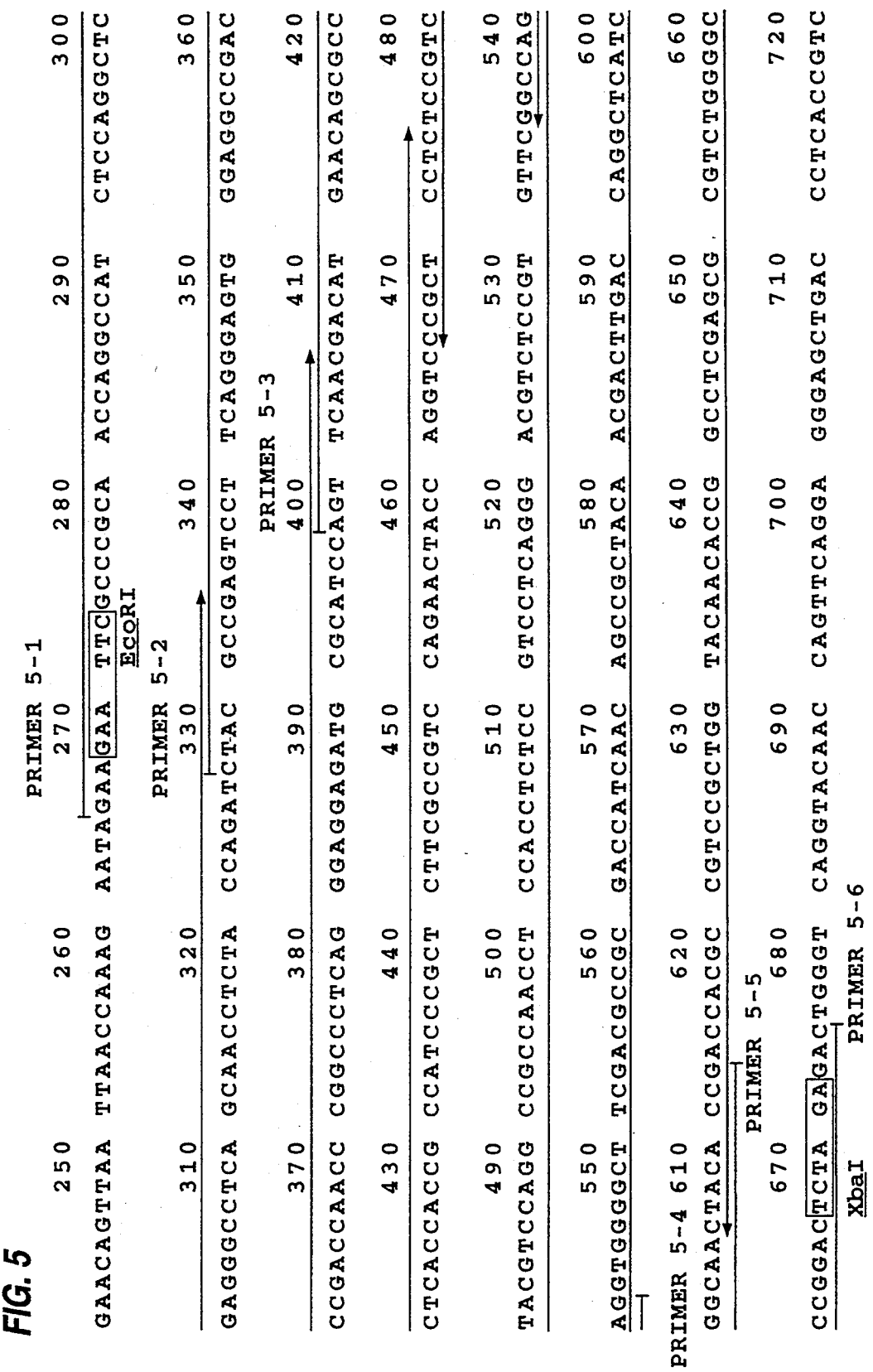
FIG. 5: A base sequence of primers (segment 5) used in PCR.

Segment 5 is a 405 bp fragment having EcoRI and XbaI sites at either end (FIG. 5). This segment was prepared according to Method B using 6 synthetic oligonucleotide primers in the same manner as noted above 1). Senseprimer 5-3 and antisenseprimer 5-4 are reacted by PCR under a similar condition to yield a 145 bp DNA. PCR was conducted using 5 μl of DNA solution containing sid 145 bp DNA, senseprimer 5-2 and antisenseprimer 5-5 to yield a 287 bp DNA. PCR using 5 μl of the 287 bp DNA-containing solution, senseprimer 5-1 and antisenseprimer 5-6 afforded the desired 411 bp double stranded DNA.

3) Preparation of Segment 4

Figure 6:
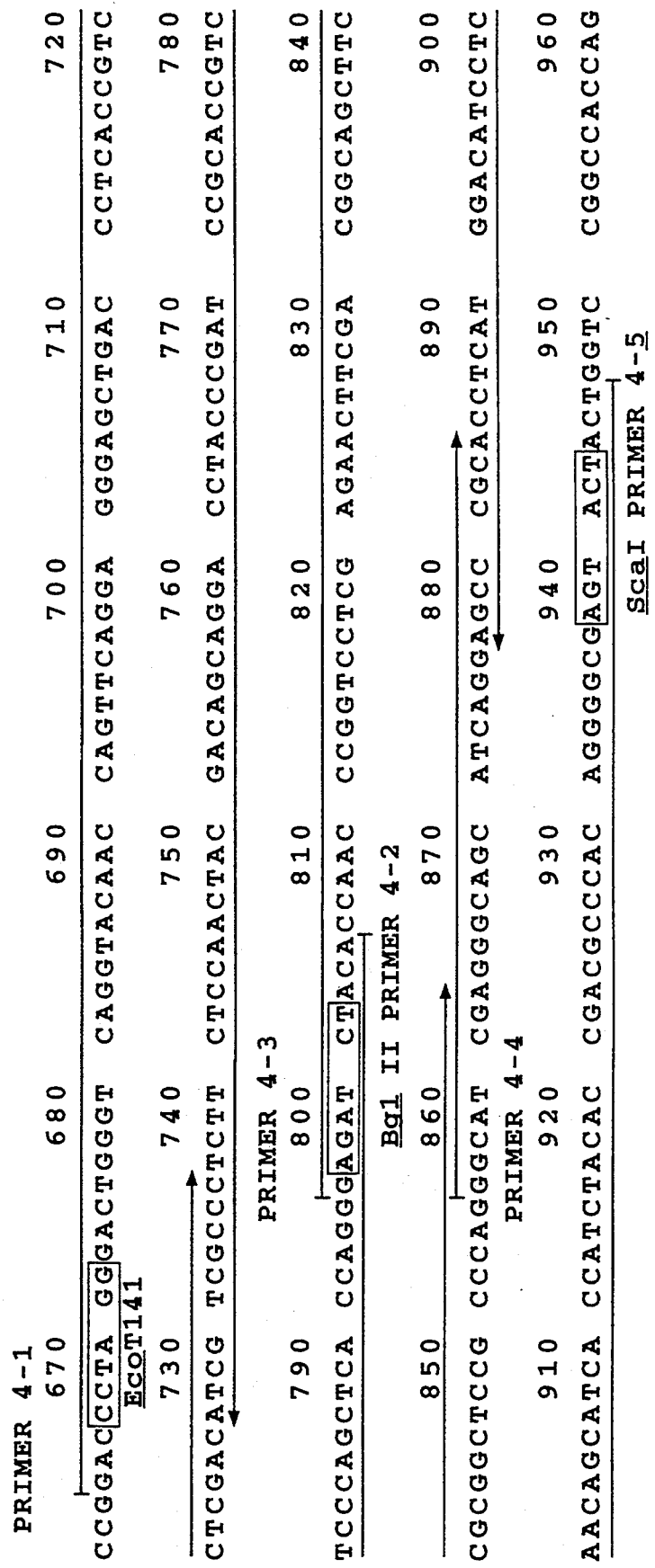
FIG. 6: A base sequence of primers (segment 4) used in PCR.

Segment 4 is a 277 bp fragment having EcoT141 and ScaI sites at either end and one internal BglII site (FIG. 6). This segment was prepared according to Methods B and C (FIGS. 2 and 3) using 5 synthetic oligonucleotide primers. Senseprimer 4-1 and antisenseprimer 4-2 are reacted by PCR to yield a 142 bp DNA having EcoT141 and BglII ends. Senseprimer 4-4 and antisenseprimer 4-5 are reacted by PCR to yield a 91 bp DNA, which is followed by another PCR using 5 μl of 91 bp DNA-containing solution, senseprimer 4-3 and antisenseprimer 4-5 to yield a 151 bp DNA having BglII and ScaI ends. Each of the 142 bp DNA and 151 bp DNA was treated as follows. The whole reaction solution containing DNA was treated with 100 μl phenol/chloroform (1:1) for the deproteinization as conventional and the aqueous layer was mixed with 10 μl of 3M NaOAc (pH 5.2) and 250 μl of EtOH to precipitate DNA. The recovered DNA was digested with 10 units restriction enzyme BglII in 100 μl solution containing 50 mM Tris-HCl (pH 7.5), 10 mMMgCl₂, 1 mM Dithiothreitol and 100 mM NaCl. The reaction mixture was electrophored on 1% Seakem GTG Agarose (FMC Inc.) in 1×TBE buffer, DNA-containing band was removed, and DNA was purified from the gel by SU-PREC-01 (Takara Inc.). About 1/10 portion from each purified DNA were used for the ligation in 50 μl reaction system in the presence of T4 DNA ligase using DNA Ligation Kit (Takara Inc.) according to the manual attached to the kit. The ligation mixture (5 μl) and senseprimer 4-1 and antisenseprimer 4-5 are subjected to PCR to yield the desired 283 bp double stranded DNA.

4) Preparation of Segment 2

Segment 2 is a 414 bp fragment having ScaI and SacI sites at either end and an internal StuI site (FIG. 7). This segment was prepared according to Methods B and C as mentioned above using 7 synthetic oligonucleotide primers. Senseprimer 2-2 and antisenseprimer 2-3 are reacted by PCR to yield a 117 bp DNA, which in turn is reacted with senseprimer 2-1 and antisenseprimer 2-3 by PCR to yield a 179 bp DNA having ScaI and StuI ends. senseprimer 2-5 and antisenseprimer 2-6 are reacted by PCR to yield a 129 bp DNA, which in turn is reacted with senseprimer 2-4 and antisenseprimer 2-7 by PCR to yield a 254 bp DNA having StuI and SacI ends. Each of 179 and 254 bp DNAs was precipitated and recovered in the same manner as mentioned in 3) above. The recovered DNAs were digested with restriction enzyme StuI in 100 μl solution containing 10 mM Tris-HCl (pH 7.5), 10 mMMgCl₂, 1 mM Dithiothreitol and 50 mM NaCl, purified and ligated in the same manner as mentioned in 3) above. PCR was carried out using the ligation mixture (5 μl) and senseprimer 2-1 and antisenseprimer 2-7 to yield the desired 420 bp double stranded DNA.

5) Preparation of Segment 6

Segment 6 is a 352 bp fragment having SacI and HindIII sites at either end (FIG. 8). This segment was prepared according to Method B (FIG. 2) in the same manner as 1) above using 5 synthetic oligonucleotide primers. Senserimer 6-3 and antisenseprimer 6-4 are reacted by PCR under a similar condition to yield a 146 bp DNA. PCR was conducted using 5 μl of DNA solution containing said 146 bp DNA, senseprimer 6-2 and antisenseprimer 6-5 to yield a 284 bp DNA. PCR using 5 μl of the 284 bp DNA-containing solution, senseprimer 6-1 and antisenseprimer 6-5 afforded the desired 354 bp double stranded DNA.

6) Preparation of Segment 3

Figure 9:
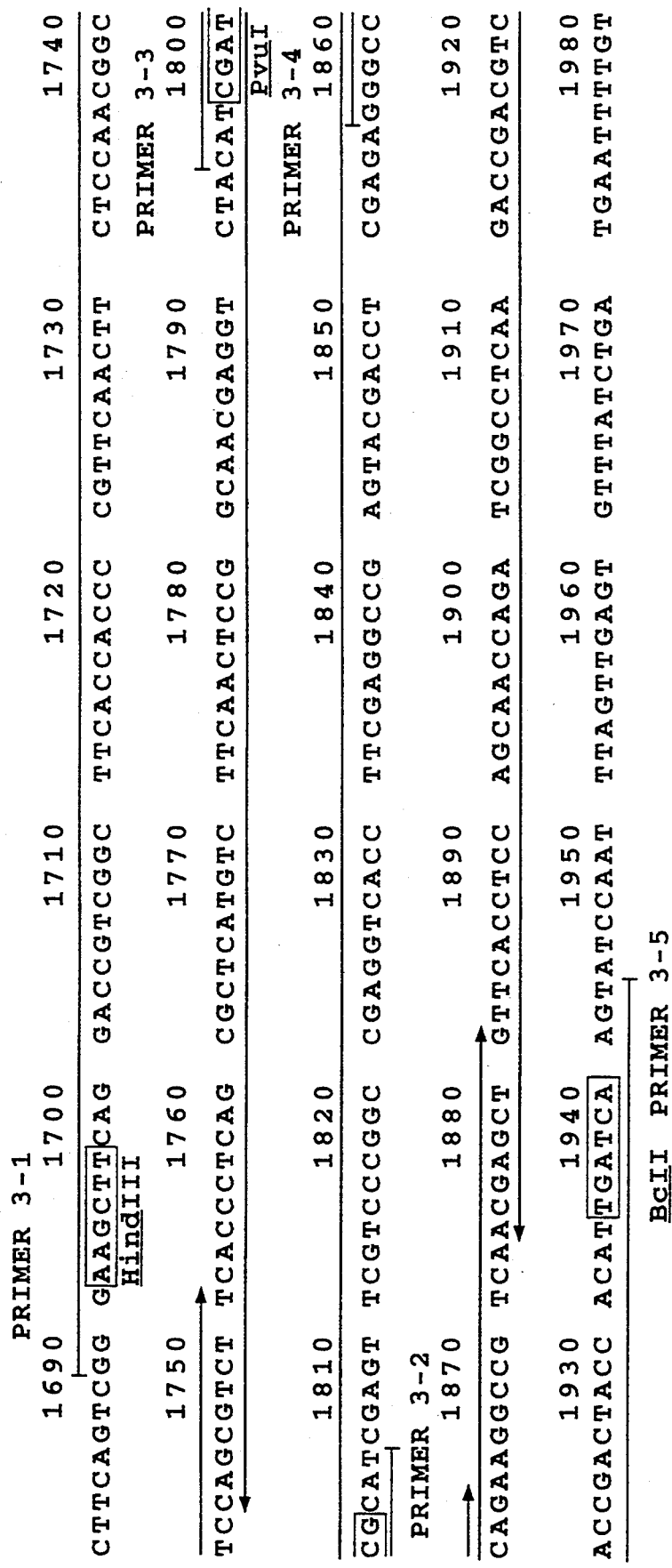
FIG. 9: A base sequence of primers (segment 3) used in PCR.

Segment 3 is a 249 bp fragment having HindIII and BclI sites at either end and an internal PvuI site (FIG. 9). This segment was prepared according to Methods B and C (FIGS. 2 and 3) as mentioned in 3) above using 5 synthetic oligonucleotide primers. Senseprimer 3-1 and antisenseprimer 3-2 are reacted by PCR to yield a 117 bp DNA having HindIII and PvuI ends. Senseprimer 3-4 and antisenseprimer 3-5 are reacted by PCR to yield a 88 bp DNA, which is reacted with senseprimer 3-3 and antisenseprimer 3-5 by PCR to yield a 150 bp DNA having PvuI and BclI ends. Each of 179 and 254 bp DNAs was precipitated in the same manner as mentioned in 3) above. The recovered DNA was digested with restriction enzyme PvuI in 100 μl solution containing 20 mM Tris-HCl (pH 8.5), 10 mM MgCl₂, 1 mM Dithiothreitol and 100 mM KCl, purified and ligated in the same manner as mentioned in 3) above. PCR was carried out using the ligation mixture (5 μl) and senseprimer 3-1 and antisenseprimer 3-5 to yield the desired 255 bp double stranded DNA.

(3) Construction of a Full Length Structural Gene Encoding *B.t.* Toxin and an Expression Vector Containing It Each of six segments obtained in (2) above was recovered, digested with restriction enzymes specific for restriction sites at both ends, fractionated and purified in a similar manner as described in (2), 3).

Thus obtained fragment was cloned in the following cloning vector using DNA Ligation Kit (Takara Inc.) and transformed into *E. coli* DH5α. Segment 1: pBSIIKS+ (Stratagene Inc.); segment 2: pMCSC8 which is derived from pHSG398 (Gene 61: 63, 1987) by digesting the plasmid pHSG398 at EcoRI and HindIII cloning sites and replacing them by preferable cloning sites as shown in FIG. 10); segment 2: pMCSA8 which is derived from pUC18 by digesting plasmid pUC18 at EcoRI and HindIII sites and replacing them by preferable cloning sites as shown in FIG. 10); segment 4: pMCSK8 which is derived from pHSG298 (Gene 61: 63, 1987) by digesting the plasmid pHSG298 at EcoRI and HindIII cloning sites and replacing them by preferable cloning sites as shown in FIG. 10); segment 5: pUC 18 (Gene 33: 103, 1985); and segment 6: pHSG399 (Gene 61: 63, 1987).

Plasmids pBTH1–6 in which segments 1–6 are cloned, respectively, were obtained by determining the base sequence of the inserted DNA (FIG. 11). The Sequencing was carried out by isolating plasmid DNA and subjecting to dideoxynucleotide sequencing method of Sanger et al (Proc. Natl. Acad. Sci. 74: 5463–5467, 1977).

Construction of plasmids was carried out as illustrated in FIG. 11. A high-expression vector pIG221 (1 μg, Tanaka et al., Nucleic Acids Research 18: 6767–6770, 1990) containing 35 S promoter derived from cauliflower mosaic virus and intron of catalase gene derived from castor-oil plant within about 1000 bp SphI-SalI region was digested with 10 units each of corresponding restriction enzymes to isolate a 1000 bp SphI-SalI fragment, which was subcloned to plasmid pHG398 to yield pBT01.

Plasmid pBTH1 which contains segment 1 was digested with restriction enzyme XbaI and blunt-ended in total 20 μl of reaction system containing T4 DNA polymerase using DNA Blunting Kit (Takara Inc.) according to the manual attached to the kit, which is followed by the digestion with SpeI to obtain a vector DNA. A part of native B.t. gene was isolated from plasmid pBT02, which contains a part (97 bp SpeI-EcoRI fragment) of native B.t. gene (originated from pSY177, J. Bacteriol. 166: 801–811, 1986) cloned in pBSIIKS+ by the digestion with restriction enzymes SpeI and EcoRV. These DNA fragments, that is, the vector DNA and a part of native B.t. gene prepared above, were ligated using DNA ligation kit (Takara Inc.) to yield plasmid pBTH101. Plasmid pBTH101 was digested with restriction enzymes salI and EcoRI to obtain a 281 bp DNA, which is then ligated to plasmid pBT01 at salI and EcoRI sites to yield plasmid pBTH111.

In a parallel experiment, plasmid pBTH112 was constructed as follows. Plasmid pBTH5 was digested with restriction enzymes EcoRI and XbaI to yield a 411 bp fragment, which was ligated to plasmid pBTH4 at restriction sites EcoRI and EcoT141, which has the same cohesive end as that of XbaI, in the same manner as noted above to yield plasmid pBTH102. Plasmid pBTH2 was digested with restriction enzymes ScaI and SacI to yield a 414 bp DNA fragment, which was ligated to plasmid pBTH102 at restriction sites ScaI and SacI in the same manner as noted above to yield plasmid pBTH112.

In another parallel experiment, about 550 bp fragment having multi stop linkers containing XbaI and SpeI sites between 238 bp BclI-KpnI fragment which contains a part of native B.t. gene (pSY177, J. Bacteriol. 166: 801–811, 1986) and about 300 bp poly (A) additional signal sequence of nopaline synthase was cloned into BclI and KpnI sites of pMCSC8 in the same manner as noted above to obtain plasmid pBT03. Plasmid pBTH3 was digested with HindIII and BclI restriction enzymes to yield 256 bp DNA fragment, which is ligated to pBT03 at HindIII and BclI sites in the same manner as noted above to yield plasmid pBTH103.

Plasmid pBTH6 was digested with restriction enzymes SacI and HindIII to yield 352 bp DNA, which is ligated to pBTH103 at SacI and HindIII sites in the same manner as noted above to yield pBTH113.

Finally, about 1300 bp SphI-EcoRI fragment of pBTH111, about 1100 bp EcoRI-SacI fragment of pBTH112, and pBTH113 were ligated at restriction sites SphI and SacI to obtain the desired full length synthetic B.t. gene and an expression vector pBT1291 (FIG. 11) capable of highly expressing said synthetic gene.

EXAMPLE 2

Expression of Synthetic Gene Encoding B.t. Toxin in Plants (1) Transformation of Protoplasts of Rice Plant The expression vector pBT1291 is used for the transformation of gramineous plants. Generally, the transformation can be carried out by suspending protoplasts originated from gramineous plants in a liquid medium, transforming said protoplasts by expression vectors carrying synthetic gene by electric pulse-treatment, incubating transformed protoplasts in an appropriate medium containing cultured cells of rice plant to obtain colonies, and regenerating recombinant plants from desired colonies by a known method (Shimamoto et al. Nature 337: 274–276, 1989).

Protoplasts were prepared as follows. A cell suspension was prepared from matured embryo callus originated from an agricultural specie of rice plant (NIPPONBARE) and grown for 3 to 5 days, when the suspension was treated in an enzyme solution (pH 5.6) containing 4% cellulase (Yakult Inc.), 1% macerozyme R-10 (Yakult Inc.) and 0.4% mannitol at 30° C. for 3–4 hr. When the enzymatic treatment completes, the culture is filtered to separate non-digested substances and the filtrate was combined with 4 times volume of KMC solution (0.118M potassium chloride, 0.0817M magnesium chloride, 0.085M calcium chloride, pH 6.0, ibid), centrifuged to pellet protoplasts and the pellet was washed twice with KMC solution.

The resultant protoplasts were suspended in a buffer (pH 5.8) containing 70 mM potassium chloride, 5 mM magnesium chloride, 0.4M mannitol and 0.1% MES at a density of $8 \times 10^6$/ml.

To the suspension were added 60 μg/ml of plasmid vector containing synthetic structural gene and 60 μg/ml of plasmid such as pGL2 (Nature 338: 274–276, 1989), which contains, as a promoter, CaMV35S and, as foreign gene(s), hygromycin phosphotransferase gene and NOS (nopaline synthase) or CaMV-originated terminator gene and cooled at 5° C. for 5 min. The mixture was transferred to a sterilized plastic cell and impressed by direct-current pulse using parallel electrode (condenser: 1000 μF; initial voltage: 500 V/cm; pulse interval: about 30 msec). The suspension was then cooled at 4° C. for 10 min, mixed with an equal amount of R2/MS protoplast agarose medium (Mol. Gen. Genet. 206: 408, 1987), and solidified at a thickness of about 0.7 mm to obtain a solid agarose (cell density, about $4 \times 10^6$/ml).

The resultant solidified agarose containing electric-pulse-treated protoplasts was cut into segments of about 10 mm large and placed in a 6 cm petri dish containing 5 ml R2/MS protoplast medium. To the dish was added about 100 mg (FW) cultured cells of rice plant as nurse cells. Cultivation of protoplasts were conducted in the dark with gentle shaking (50 rpm) at about 29° C. for about 10 days.

Cultured cells were prepared as follows. Calluses prepared from roots of rice plants raised from seeds were subcultured in a liquid medium every week to obtain suspension of cultured cells, and fine cells (1 mmφ) which were actively dividing were selected from the suspension.

After 10-day-incubation, nurse cells were removed by KMC solution and incubation was continued for 2–4 days, when 20 μg/ml of hygromycin B was added and incubation was continues for additional 2–3 weeks.

A piece of agarose was transferred to R2 soft agar medium containing 2 mg/l of 2,4-dichlorophenoxyacetic acid (2,4-D), 6% sucrose, and 0.25% agarose and the mixture incubated for 2–4 weeks to allow the colonies grow. Enlarged colonies were separated and transferred to R2 soft agar medium.

When the resultant callus was transferred to R2/MS regenerating medium (3% sorbitol, 2% sucrose, 1% agarose, pH 5.8) and incubated with lighting (2000–4000 lux) at 25° C. for 3–10 weeks, regeneration of shoot and root were observed. When the shoot grew to about 2 cm, it was transferred to a plastic box containing R2/MS regenerating medium and grown to a young plant. It was further grown in vermiculite-pot to obtain a matured recombinant rice plant.

(2) Screening of Transformants by PCR

Hygromycin-resistant colonies were screened for the presence of transformed synthetic gene as follows. DNA was extracted from a part of hygromycin-resistant colonies (Mol. Gen. Genet. 211: 27, 1988). Two calluses were homogenized in 250 μl of Resuspension Buffer (20 mM Tris-HCl, 10 mM EDTA) in a 1.5 ml microcentrifuging tube. To the homogenate was added 20 μl of 20% SDS and incubated at 68° C. for 15 min. After the addition of 150 μl of 7.5M ammonium acetate, the mixture was placed on ice for 30 min and centrifuged at 15000 rpm, 4° C. for 15 min. To the supernatant was added 1 ml EtOH and centrifuged under the same conditions to precipitate DNA. The DNA was washed with 70% EtOH, dried and dissolved in 30μl of TB buffer (10 mM Tris-HCl, pH 8.0, 1 mM EDTA).

Figure 12:
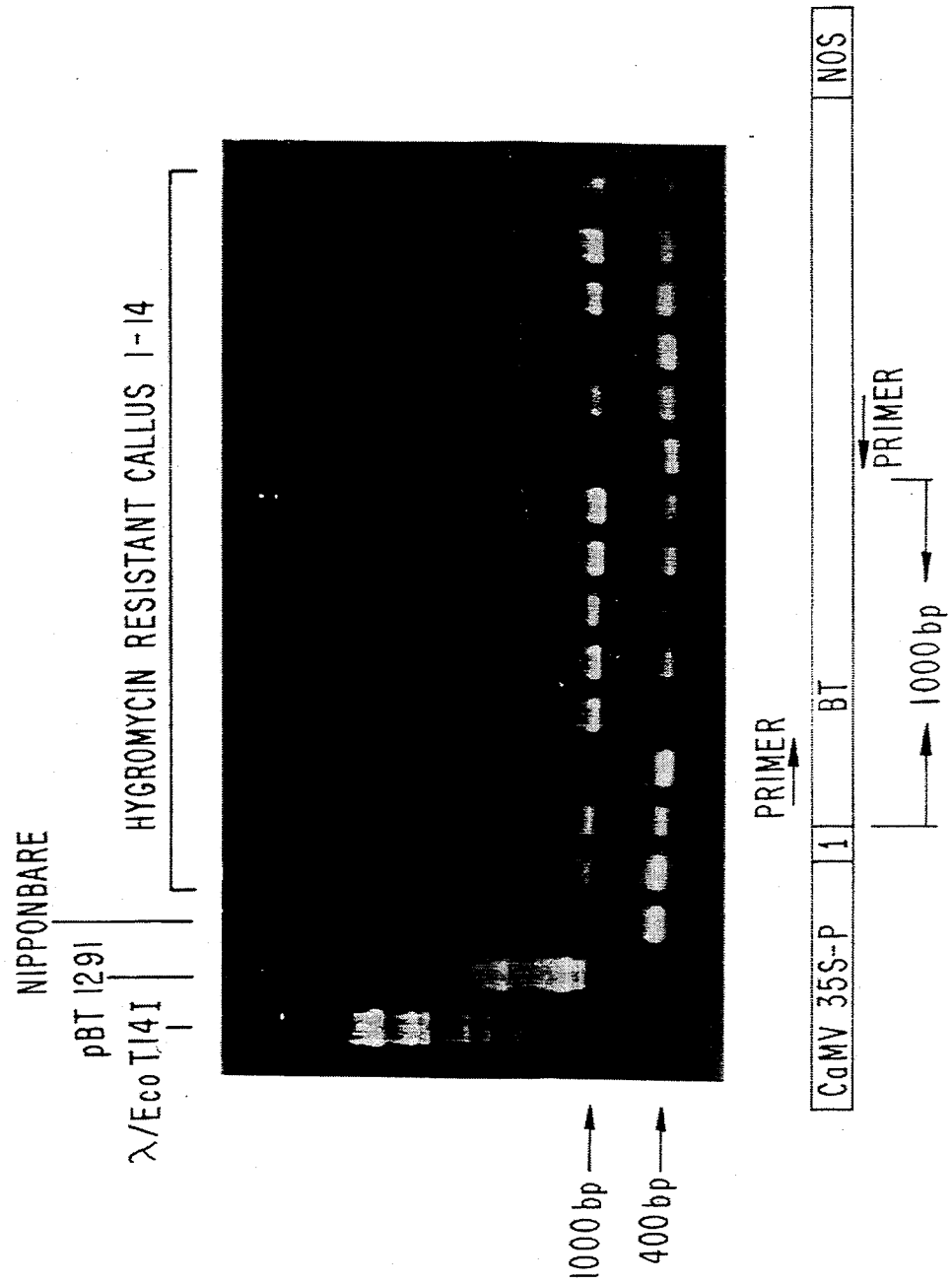
FIG. 12: A migration pattern obtained when PCR products were subjected to electrophoresis for the screening of transformants.

Thus obtained DNA was subjected to PCR for the screening of transformed genes using primers shown in FIG. 12. PCR was carried out in total 50 μl of reaction mixture containing 5 μl of DNA obtained above, 1 μM each of primers, 10 mM Tris-HCl (pH 8.3), 1.5 mM $MgCl_2$, 50 mM KCl, 0.005% Tween 20, 0.005% NP-40, 0.001% Gelatin, 200 μM each of dATP, dGTP, dCTP and dTTP, and 5 units REPLITHERM Thermostable DNA Polymerase (EPISENTRE Inc.). PCR was conducted by repeating 30–35 times of reaction cycles comprising: 94° C., 1 min, 50° C., 2 min and 72° C., 3 min in DNA Thermal Cycler PJ1000 (PERKIN-ELMER CETUS Inc.) and the products were analyzed conventionally by electrophoresis. As can be seen from FIG. 12, a 1.0 kb band of amplified DNA was observed in case of callus transformed by plasmid pBT1291. Many hygromycin-resistant colonies were screened in the same manner and 47% of them were proved to contain the synthetic gene (plasmid pBT1291).

(3) Detection of a Full-Length Transformed Gene

Figure 13:
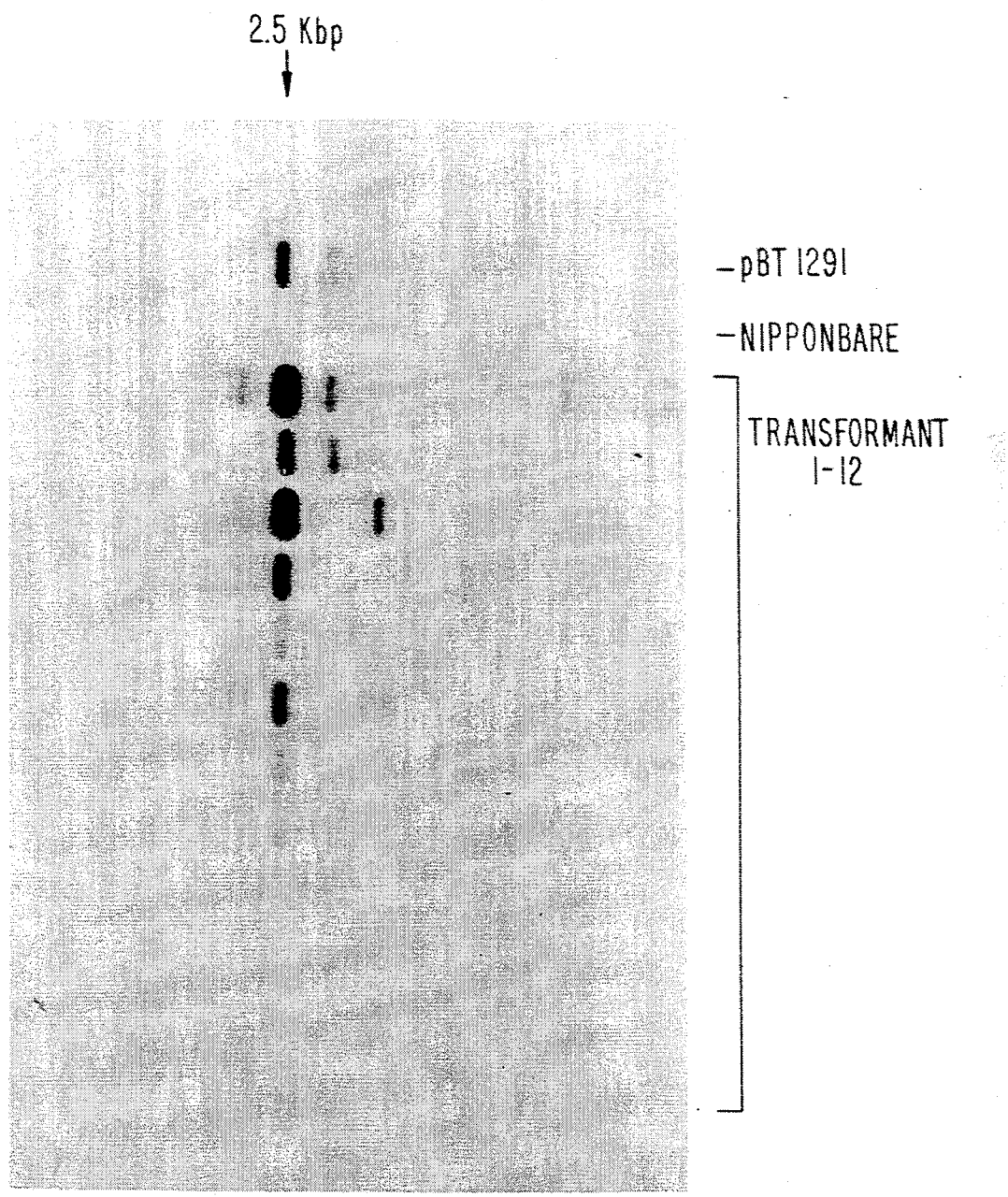
FIG. 13: A migration pattern obtained when the gene used for the transformation was detected by Southern hybridization.
Figure 14:
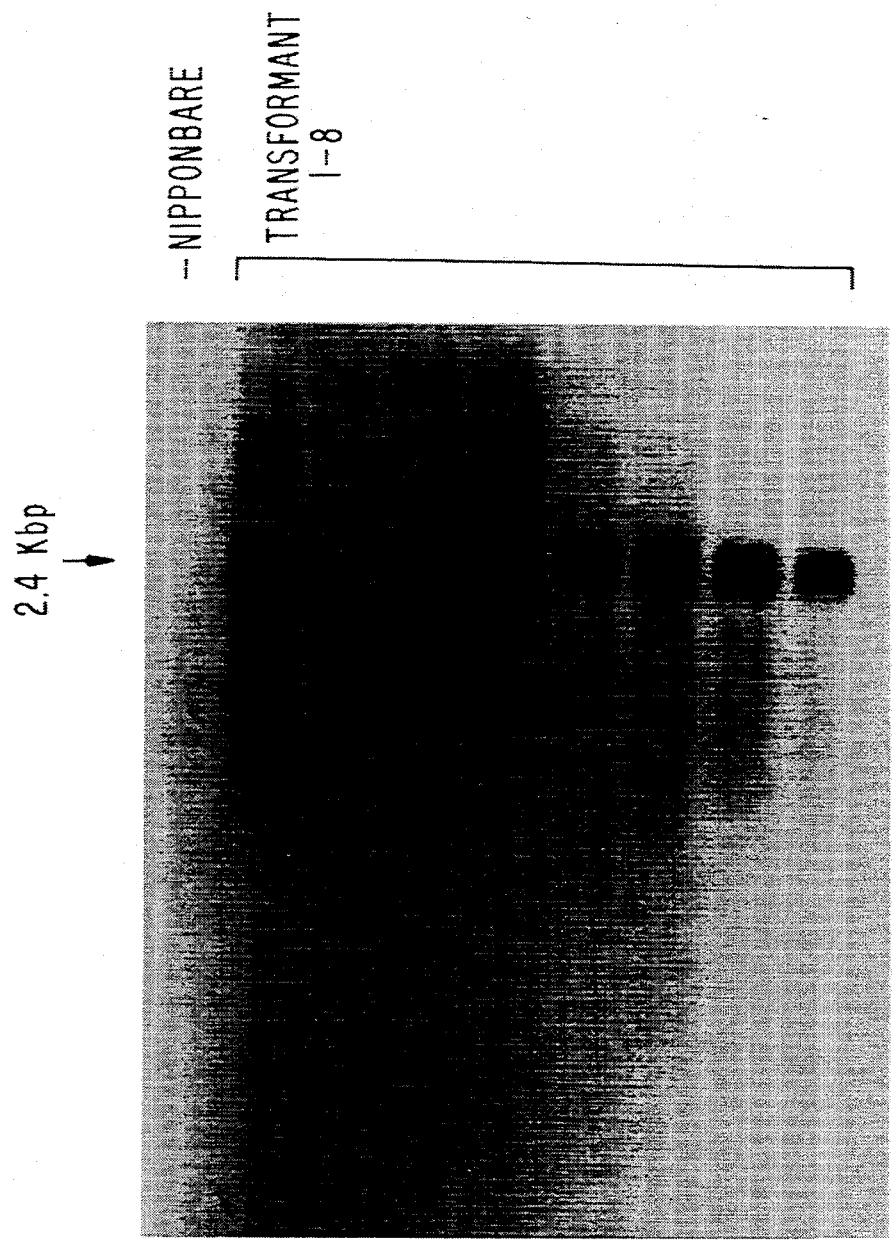
FIG. 14: A migration pattern obtained when the mRNA for the gene used for the transformation was detected by Northern hybridization.
Figure 15:
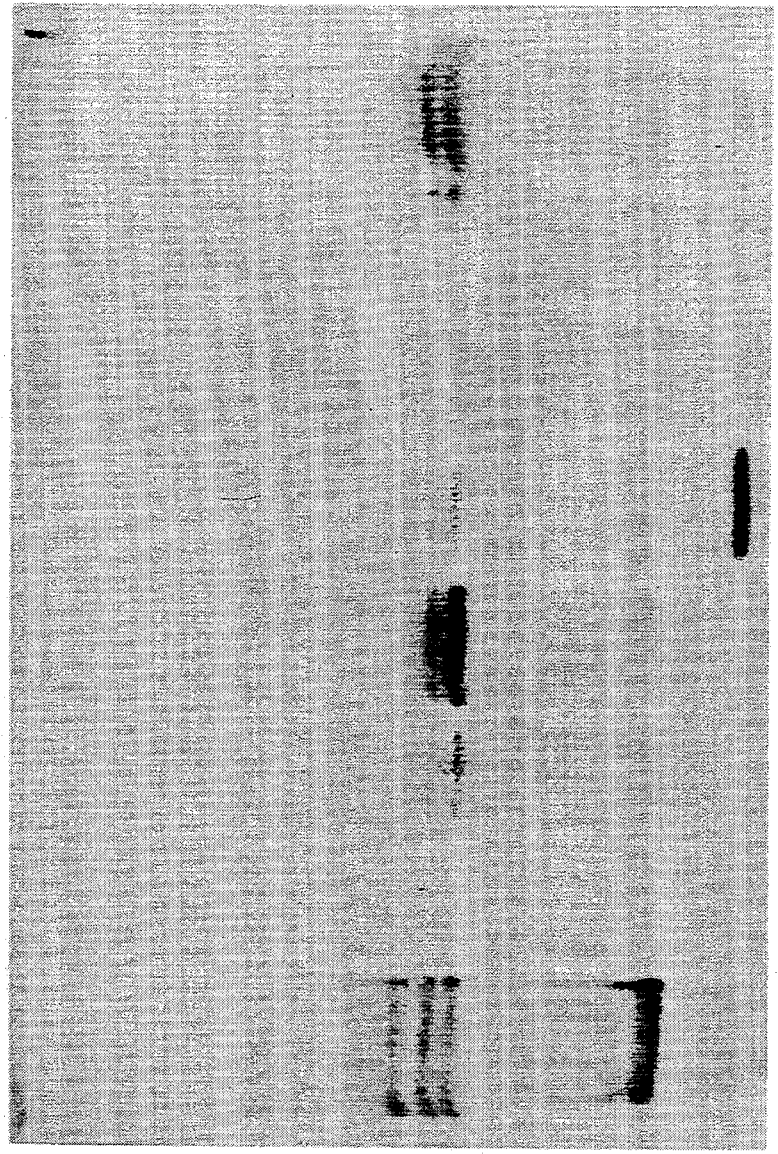
FIG. 15: A migration pattern obtained when the expressed $B.t.$ toxin protein in transgenic rice leaves was detected by Western blotting.
Figure 19:
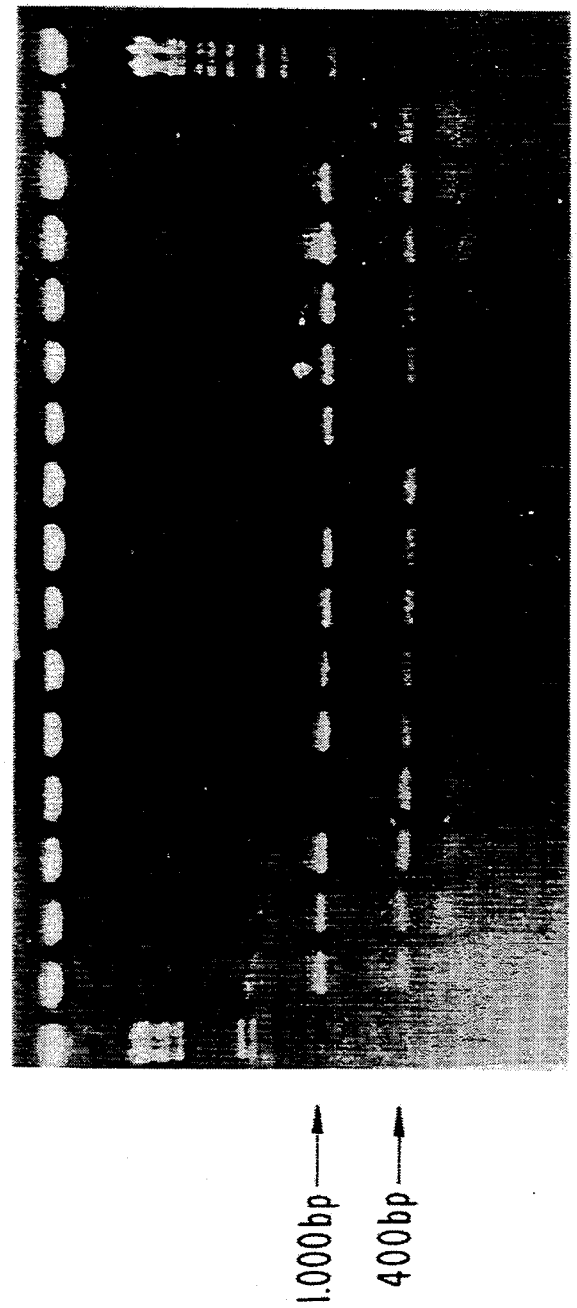
FIG. 19: A migration pattern obtained when PCR products of the secondary generation of transformants were electrophoresed.
Figure 20:
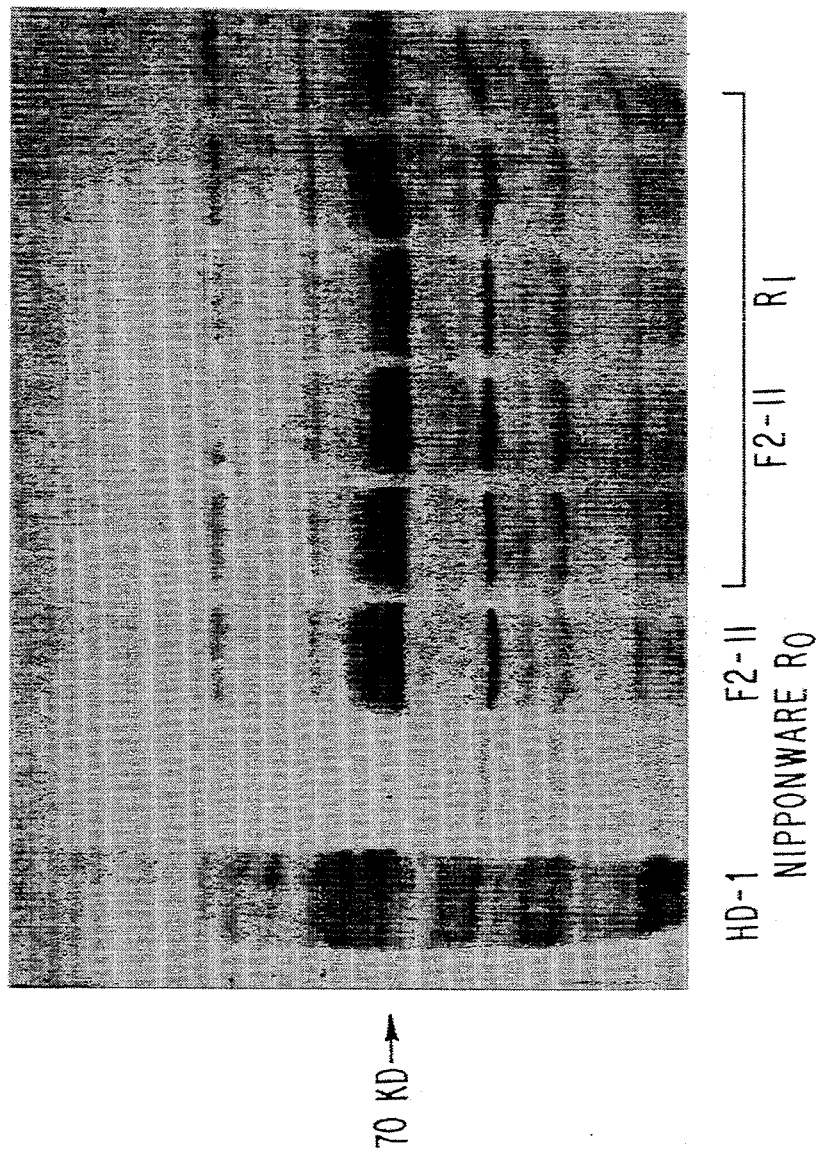
FIG. 20: A migration pattern obtained when the expressed $B.t.$ toxin protein in the leaves of the secondary generation ($R_1$) was detected by Western blotting.

DNA was extracted from transformed callus obtained by the screening of (2) above, digested with 20 units restriction enzyme XbaI and analyzed by Southern hybridization (J. Mol. Biol. 98: 505, 1980). XbaI fragment of pBT1291 was labeled using Multi-prime DNA Labeling System (Amersham Inc., Feinberg et al. Analytical Biochem. 137: 266–267, 1987) and α-$^{32}$P-dCTP (Amersham Inc., 370 MBq/ml, 110 TBq/mmol) and used as probe. Results are given in FIG. 13., which shows that a predicted 2.5 kb DNA band corresponding to a combined length of B.t. synthetic gene and intron was detected in all transformed subjects.

(4) Detection of mRNA as the Transcript of Transformed Gene

Total RNA was isolated from transformed callus which was confirmed to contain the full length gene by Southern hybridization (Analytical Biochem. 162: 156–159, 1987). Each RNA (20 μg) was analyzed by Northern hybridization (Thomas, P. et al. Proc. Natl. Acad. Sci. 77: 5201, 1980) using a probe prepared in the same manner as noted above. The results are given in FIG. 14, which shows that 3.0–2.4 kb band of mRNA corresponding to a predicted transcript of the transformed gene are detected in all subjects.

(5) Detection of *B.t.* Toxin as the Translation Product of Transformed Gene

SDS soluble protein was extracted from leaves of regenerated rice plants and used for the detection of *B.t.* toxin by Western blotting (Towbin et al. Proc. Natl. Acad. Sci. 76: 4350, 1979). A piece (about 2×0.5 cm) of leaf of recombinant rice plant was lyophilized with liquid nitrogen and ground in a mortar to a powder, which was immediately extracted with 100 μl of 2×sample buffer (25 mM Tris-HCl, pH 6.8, 4% SDS, 8 mM DTT, 20% glycerol, 0.004% BPB, 200 uM leupepsin). The extract was heated in a boiling bath for 5 min, centrifuged at 12000 rpm, 4° C. for 15 min to separate the supernatant as a sample solution. The sample solution was applied to SDS-PAGE electrophoresis and transferred to Immobilon Membrane (MILLIPORE Inc.) in Blotting buffer (25 mM Tris, 192 mM Glycine, 20% MeOH) at 200 mA, 35 V, over 1 hr. In the detection of *B.t.* toxin were used immunoglobulin G (IgG) purified from anti-*B.t.* toxin antiserum raised in immunized rabbit as the primary antibody and alkaline phosphatase-conjugated goat anti-rabbit IgG (JACKSON Inc.) as the secondary antibody.

Results are shown in FIG. 15, which shows that a protein of a molecular weight of about 72 kD capable of reacting with immunoglobulin G (IgG) purified from antiserum raised against *B.t.* toxin was detected. The expression of this protein was estimated to be about 0.05%–0.1% of that of SDS-soluble proteins.

(6) Inheritance of Synthetic Gene to the Next Generation $R_1$ and Expression Thereof Seeds were collected from rice plants which express *B.t.* toxin highly, sowed and grown for the detection of the inheritance of the synthetic gene to the next generation ($R_1$) and the ratio of segregation. DNA was extracted from a leaf (about 5×2 mm) of plants 14 days after the sowing in a similar manner as mentioned above in (2) and subjected to PCR. The results are shown in Table 1, which indicates that the gene is inherited in three independent lines and the ratio of segregation is about 3:1. DNA extracted from plants of C7-4 line was analyzed by electrophoresis (FIG. 19).

TABLE 1

| Line of $R_1$ | B.t.+ | B.t.− |
|---|---|---|
| B2-9 | 98 | 28 |
| C7-4 | 26 | 10 |
| F2-11 | 17 | 6 |

Western blotting was carried out using about 3-month-old plants of F2-11 line in the same manner as mentioned above in (5), which revealed that the plant of $R_1$ generation also expresses *B.t.* toxin to approximately the same extent as plants of parent generation (FIG. 20).

(7) Insect-resistance Test of Recombinant Plants

The resistance of recombinant plants against typical pests for rice plant, *Cnaphalocrocis medinalis* belonging to Lepidoptera, was examined as follows. In the test, the survival rate (or death rate) of pests inoculated to a rice plant was examined using 14-day-old seedlings of a line proved to inherit the full length synthetic gene (*B.t.*-gene (+)) such as B2-9 line (test group).

Roots of 14-day-old seedlings of B2-9 line were washed thoroughly and wrapped with absorbent cotton moistened with water, which was again wrapped with parafilm to prevent water from evaporating to keep the plant alive One plant was placed in a semi-transparent plastic tube of about 20 cm high and a 2-day-old *C. medinails* (2–3 mm) was inoculated thereto. The test was carried out for 7 days at 25° C. adjusting the day and night interval to 12 hr each. In the same test, rice plants that have not treated (native plant, NIPPONBARE) and that have treated with the expression vector of the invention but lost *B.t.* gene as the result of segregation (*B.t.*-gene(−)) were used as controls in the same manner. The results are given in Tables 2 and 3 below. The survival rate (or death rate) of pests in test group (B.t.-gene(+)), is quite different from those in control groups (NIPPONBARE and B.t.-gene(−)). That is, the death rate observed in test group is higher than those observed in control groups. It is also apparent that the growth rate of pests survived is lower in test group compared to control groups.

TABLE 2

| | Growth Stage of *C. medinalis* | | | | | | Mean weight of pests survived |
|---|---|---|---|---|---|---|---|
| | die | 2 | 3 | 4 | 5 | 6* | |
| NIPPONBARE | 1 | 1 | 4 | 8 | 8 | 7 | 3.75 mg |
| B.t. gene(−) | | | 1 | 4 | 3 | | 3.13 mg |
| B.t. gene(+) | 10 | | 3 | 10 | 8 | | 2.67 mg |

TABLE 3

| | Growth Stage of *C. medinalis* | | Mean weight of pests survived |
|---|---|---|---|
| | die | 4* | |
| NIPPONBARE | 5 | 5 | 1.48 mg |
| B.t. gene(−) | 4 | 4 | 1.58 mg |
| B.t. gene(+) | 20 | 4 | 1.0 mg |

*: each figure represents the stage (2-6), and figures under them represent the number of pests survived until the respective stage.

It is apparent from the above, rice plants expressing the transformed B.t. toxin-encoding gene to high extent can resist against pests belonging to Lepidoptera effectively.

In conclusion, because the synthetic gene of the present invention encodes B.t. toxin and has a base sequence fitted to gramineous plants, it can be expressed highly in gramineous plants and afford plants resistance against pests. The resultant recombinant rice plants of the invention are expected to be agriculturally useful.

What we claim is:

1. A synthetic gene encoding an insecticidal protein, wherein said gene has the base sequence shown in SEQ ID No. 1.

2. A vector which contains a promoter functional in gramineous plants, a structural gene as claimed in claim 1 and a terminator located downstream from said promoter, the promoter and the terminator being operably linked to the structural gene.

3. A recombinant plant of the genus Oryza produced by transforming the vector as claimed in claim 2 into protoplasts derived from plants of the genus Oryza, growing said protoplasts to form colonies, and regenerating plants from said colonies.

4. A method for producing recombinant plants of the genus Oryza which comprises suspending vectors as claimed in claim 2 and protoplasts derived from plants of the genus Oryza in a liquid medium, impressing an electric pulse to transform vectors into protoplasts, incubating said protoplasts in a medium containing cultured cells of rice plants to form colonies, selecting transformed colonies from said colonies, and regenerating plants from said colonies.

* * * * *